(12) United States Patent
Nolte et al.

(10) Patent No.: US 7,910,356 B2
(45) Date of Patent: Mar. 22, 2011

(54) MULTIPLEXED BIOLOGICAL ANALYZER PLANAR ARRAY APPARATUS AND METHODS

(75) Inventors: David D. Nolte, Lafayette, IN (US); Manoj Varma, West Lafayette, IN (US); Fred E. Regnier, West Lafayette, IN (US); Leilei Peng, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 191 days.

(21) Appl. No.: 11/345,477

(22) Filed: Feb. 1, 2006

(65) Prior Publication Data
US 2007/0003925 A1    Jan. 4, 2007

Related U.S. Application Data

(60) Provisional application No. 60/649,043, filed on Feb. 1, 2005.

(51) Int. Cl.
*C12M 1/34* (2006.01)
(52) U.S. Cl. ......... 435/288.7; 435/6; 435/7.1; 435/7.92; 436/518; 427/2.12; 427/466
(58) Field of Classification Search .............. 422/82.05, 422/82.09, 64; 436/45, 165, 518; 356/73
See application file for complete search history.

(56) References Cited

U.S. PATENT DOCUMENTS
3,796,495 A    3/1974    Laub
(Continued)

FOREIGN PATENT DOCUMENTS
EP    1189062 A1    3/2002
(Continued)

OTHER PUBLICATIONS

Nolte et al., Spinning-Disk Interferometry: the bioCD, Oct. 2004, Optics&Photonics News, 15(10): pp. 48-53.*
(Continued)

*Primary Examiner* — Nelson Yang
(74) *Attorney, Agent, or Firm* — Baker & Daniels LLP (57) ABSTRACT

A planar array having plurality of biological recognition molecules including at least two types of biological recognition molecules distributed about a substrate is disclosed. A first type of biological recognition molecules is distributed according to a first frequency and a second type of biological recognition molecules is distributed according to a second frequency. Another planar array having a plurality of biological recognition molecules including at least two kinds of biological recognition molecules is disclosed. The recognition molecules are distributed about a substrate with first kind of biological recognition molecules distributed at a first height or depth relative to a surface of the substrate and a second kind of biological recognition molecules distributed at a second height or depth relative to the surface. An apparatus including a surface normal interferometry platform including a scanning pathway and a plurality of analyzer molecules adapted to detect the presence or absence of a plurality of target analytes is also disclosed. The plurality of analyzer molecules are distributed about the scanning pathway according to a multiplexing scheme. A method including multiplexing a plurality of kinds of capture molecules about a detection pathway is further disclosed. The method also includes contacting a biological sample to the array, detecting the presence or absence of binding of the plurality of kinds of capture molecules and a plurality of target analytes using interferometry.

19 Claims, 7 Drawing Sheets

U.S. PATENT DOCUMENTS

| | | |
|---|---|---|
| 4,537,861 A | 8/1985 | Elings et al. |
| 4,649,529 A | 3/1987 | Avicola |
| 4,741,620 A | 5/1988 | Wickramasinghe |
| 4,876,208 A | 10/1989 | Gustafson et al. |
| 4,899,195 A | 2/1990 | Gotoh |
| 4,975,237 A | 12/1990 | Brown |
| RE33,581 E | 4/1991 | Nicoli et al. |
| 5,122,284 A | 6/1992 | Braynin et al. |
| 5,155,549 A | 10/1992 | Dhadwal |
| 5,413,939 A * | 5/1995 | Gustafson et al. ............ 436/518 |
| 5,478,527 A | 12/1995 | Gustafson et al. |
| 5,478,750 A | 12/1995 | Bernstein et al. |
| 5,491,550 A | 2/1996 | Dabbs |
| 5,494,829 A | 2/1996 | Sandstrom et al. |
| 5,497,007 A | 3/1996 | Uritsky et al. |
| 5,545,531 A | 8/1996 | Rava et al. |
| 5,578,499 A * | 11/1996 | Ismail ........................... 436/524 |
| 5,581,345 A | 12/1996 | Oki et al. |
| 5,602,377 A | 2/1997 | Beller et al. |
| 5,621,532 A | 4/1997 | Ooki et al. |
| 5,629,044 A | 5/1997 | Rubenchik |
| 5,631,171 A | 5/1997 | Sandstrom et al. |
| 5,653,939 A | 8/1997 | Hollis et al. |
| 5,700,046 A | 12/1997 | Van Doren et al. |
| 5,717,778 A | 2/1998 | Chu et al. |
| 5,736,257 A | 4/1998 | Conrad et al. |
| 5,781,649 A | 7/1998 | Brezoczky |
| 5,786,226 A | 7/1998 | Bocker et al. |
| 5,837,475 A | 11/1998 | Dorsel et al. |
| 5,843,767 A | 12/1998 | Beattie |
| 5,844,871 A | 12/1998 | Maezawa |
| 5,874,219 A | 2/1999 | Rava et al. |
| 5,875,029 A | 2/1999 | Jann et al. |
| 5,883,717 A | 3/1999 | DiMarzio et al. |
| 5,892,577 A | 4/1999 | Gordon |
| 5,900,935 A | 5/1999 | Klein et al. |
| 5,922,617 A | 7/1999 | Wang et al. |
| 5,935,785 A | 8/1999 | Reber et al. |
| 5,945,344 A | 8/1999 | Hayes et al. |
| 5,955,377 A | 9/1999 | Maul et al. |
| 5,968,728 A | 10/1999 | Perttunen et al. |
| 5,999,262 A | 12/1999 | Dobschal et al. |
| 6,008,892 A | 12/1999 | Kain et al. |
| 6,030,581 A | 2/2000 | Virtanen |
| 6,048,692 A | 4/2000 | Maracas et al. |
| 6,060,237 A | 5/2000 | Nygren et al. |
| 6,071,748 A | 6/2000 | Modlin et al. |
| 6,099,803 A | 8/2000 | Ackley |
| 6,110,748 A | 8/2000 | Reber et al. |
| 6,121,048 A | 9/2000 | Zaffaroni et al. |
| 6,140,044 A | 10/2000 | Besemer et al. |
| 6,143,247 A | 11/2000 | Sheppard, Jr. et al. |
| 6,177,990 B1 | 1/2001 | Kain et al. |
| 6,221,579 B1 | 4/2001 | Everhart et al. |
| 6,238,869 B1 | 5/2001 | Kris et al. |
| 6,248,539 B1 | 6/2001 | Ghadiri et al. |
| 6,249,593 B1 | 6/2001 | Chu et al. |
| 6,256,088 B1 | 7/2001 | Gordon |
| 6,271,924 B1 | 8/2001 | Ngoi et al. |
| 6,287,783 B1 | 9/2001 | Maynard et al. |
| 6,287,850 B1 | 9/2001 | Besemer et al. |
| 6,312,901 B2 | 11/2001 | Virtanen |
| 6,312,961 B1 | 11/2001 | Voirin et al. |
| 6,319,468 B1 | 11/2001 | Sheppard, Jr. et al. |
| 6,319,469 B1 | 11/2001 | Mian et al. |
| 6,320,665 B1 | 11/2001 | Ngoi et al. |
| 6,327,031 B1 | 12/2001 | Gordon |
| 6,339,473 B1 | 1/2002 | Gordon |
| 6,342,349 B1 | 1/2002 | Virtanen |
| 6,342,395 B1 | 1/2002 | Hammock et al. |
| 6,345,115 B1 | 2/2002 | Ramm et al. |
| 6,350,413 B1 | 2/2002 | Reichert et al. |
| 6,355,429 B1 | 3/2002 | Nygren et al. |
| 6,368,795 B1 | 4/2002 | Hefti |
| 6,376,258 B2 | 4/2002 | Hefti |
| 6,381,025 B1 | 4/2002 | Bornhop et al. |
| 6,387,331 B1 | 5/2002 | Hunter |
| 6,395,558 B1 | 5/2002 | Duveneck et al. |
| 6,395,562 B1 | 5/2002 | Hammock et al. |
| 6,399,365 B2 | 6/2002 | Besemer et al. |
| 6,403,957 B1 | 6/2002 | Fodor et al. |
| 6,416,642 B1 | 7/2002 | Alajoki et al. |
| 6,469,787 B1 | 10/2002 | Meyer et al. |
| 6,476,907 B1 | 11/2002 | Gordon |
| 6,483,585 B1 | 11/2002 | Yang |
| 6,483,588 B1 | 11/2002 | Graefe et al. |
| 6,496,267 B1 | 12/2002 | Takaoka |
| 6,496,309 B1 | 12/2002 | Bliton et al. |
| 6,504,618 B2 | 1/2003 | Morath et al. |
| 6,518,056 B2 | 2/2003 | Schembri et al. |
| 6,551,817 B2 | 4/2003 | Besemer et al. |
| 6,566,069 B2 | 5/2003 | Virtanen |
| 6,584,217 B1 | 6/2003 | Lawless et al. |
| 6,591,196 B1 | 7/2003 | Yakhini et al. |
| 6,596,483 B1 | 7/2003 | Choong et al. |
| 6,602,702 B1 | 8/2003 | McDevitt et al. |
| 6,623,696 B1 | 9/2003 | Kim et al. |
| 6,624,896 B1 | 9/2003 | Neal et al. |
| 6,649,403 B1 | 11/2003 | McDevitt et al. |
| 6,653,152 B2 | 11/2003 | Challener |
| 6,656,428 B1 | 12/2003 | Clark et al. |
| 6,685,885 B2 * | 2/2004 | Nolte et al. ..................... 422/64 |
| 6,687,008 B1 | 2/2004 | Peale et al. |
| 6,709,869 B2 | 3/2004 | Mian et al. |
| 6,720,177 B2 | 4/2004 | Ghadiri et al. |
| 6,733,977 B2 | 5/2004 | Besemer et al. |
| 6,734,000 B2 | 5/2004 | Bhatia |
| 6,737,238 B2 | 5/2004 | Suzuki et al. |
| 6,743,633 B1 | 6/2004 | Hunter |
| 6,760,298 B2 | 7/2004 | Worthington et al. |
| 6,766,817 B2 | 7/2004 | da Silva |
| 6,770,447 B2 | 8/2004 | Maynard et al. |
| 6,783,938 B2 | 8/2004 | Nygren et al. |
| 6,787,110 B2 | 9/2004 | Tiefenthaler |
| 6,791,677 B2 | 9/2004 | Kawai et al. |
| 6,803,999 B1 | 10/2004 | Gordon |
| 6,806,963 B1 | 10/2004 | Walti et al. |
| 6,819,432 B2 | 11/2004 | Pepper et al. |
| 6,836,338 B2 | 12/2004 | Opsal et al. |
| 6,844,965 B1 | 1/2005 | Engelhardt |
| 6,847,452 B2 | 1/2005 | Hill |
| 6,878,555 B2 | 4/2005 | Anderson et al. |
| 6,891,791 B1 | 5/2005 | Gutin |
| 6,897,965 B2 | 5/2005 | Ghadiri et al. |
| 6,917,421 B1 | 7/2005 | Wihl et al. |
| 6,917,432 B2 | 7/2005 | Hill et al. |
| 6,918,404 B2 | 7/2005 | da Silva |
| 6,937,323 B2 | 8/2005 | Worthington et al. |
| 6,955,878 B2 | 10/2005 | Kambara et al. |
| 6,958,131 B2 | 10/2005 | Tienfenthaler |
| 6,980,299 B1 | 12/2005 | de Boer |
| 6,980,677 B2 | 12/2005 | Niles et al. |
| 6,987,569 B2 | 1/2006 | Hill |
| 6,990,221 B2 | 1/2006 | Shams |
| 6,992,769 B2 | 1/2006 | Gordon |
| 6,995,845 B2 | 2/2006 | Worthington |
| 7,008,794 B2 | 3/2006 | Goh et al. |
| 7,012,249 B2 | 3/2006 | Krutchinsky et al. |
| 7,014,815 B1 | 3/2006 | Worthington et al. |
| 7,026,131 B2 | 4/2006 | Hurt et al. |
| 7,027,163 B2 | 4/2006 | Angeley |
| 7,031,508 B2 | 4/2006 | Lawless et al. |
| 7,033,747 B2 | 4/2006 | Gordon |
| 7,061,594 B2 | 6/2006 | Worthington et al. |
| 7,070,987 B2 | 7/2006 | Cunningham et al. |
| 7,077,996 B2 | 7/2006 | Randall et al. |
| 7,083,920 B2 | 8/2006 | Werner et al. |
| 7,087,203 B2 | 8/2006 | Gordon et al. |
| 7,088,650 B1 | 8/2006 | Worthington et al. |
| 7,091,034 B2 | 8/2006 | Virtanen |
| 7,091,049 B2 | 8/2006 | Boga et al. |
| 7,094,609 B2 | 8/2006 | Demers |
| 7,098,041 B2 | 8/2006 | Kaylor et al. |
| 7,102,752 B2 | 9/2006 | Kaylor et al. |
| 7,106,513 B2 | 9/2006 | Moon et al. |
| 7,110,094 B2 | 9/2006 | Gordon |
| 7,110,345 B2 | 9/2006 | Worthington et al. |

| | | |
|---|---|---|
| 7,118,855 B2 | 10/2006 | Cohen et al. |
| 7,141,378 B2 | 11/2006 | Miller et al. |
| 7,141,416 B2 | 11/2006 | Krutzik |
| 7,145,645 B2 | 12/2006 | Blumenfeld et al. |
| 7,148,970 B2 | 12/2006 | de Boer |
| 7,200,088 B2 | 4/2007 | Worthington et al. |
| 7,221,632 B2 | 5/2007 | Worthington |
| 2001/0055812 A1 | 12/2001 | Mian et al. |
| 2002/0001546 A1 | 1/2002 | Hunter et al. |
| 2002/0008871 A1 | 1/2002 | Poustka et al. |
| 2002/0045276 A1 | 4/2002 | Yguerabide et al. |
| 2002/0051973 A1 | 5/2002 | Delenstarr et al. |
| 2002/0058242 A1* | 5/2002 | Demers ............... 435/4 |
| 2002/0085202 A1 | 7/2002 | Gordon |
| 2002/0097658 A1 | 7/2002 | Worthington et al. |
| 2002/0106661 A1 | 8/2002 | Virtanen |
| 2002/0127565 A1 | 9/2002 | Cunningham et al. |
| 2002/0135754 A1 | 9/2002 | Gordon |
| 2002/0151043 A1 | 10/2002 | Gordon |
| 2002/0192664 A1 | 12/2002 | Nygren et al. |
| 2003/0026735 A1 | 2/2003 | Nolte et al. |
| 2003/0035352 A1 | 2/2003 | Worthington |
| 2003/0054376 A1 | 3/2003 | Mullis et al. |
| 2003/0112446 A1 | 6/2003 | Miller et al. |
| 2003/0133640 A1 | 7/2003 | Tiefenthaler |
| 2003/0134330 A1 | 7/2003 | Ravkin et al. |
| 2004/0002085 A1 | 1/2004 | Schembri et al. |
| 2004/0058455 A1* | 3/2004 | Grier et al. ............ 436/518 |
| 2004/0078337 A1 | 4/2004 | King et al. |
| 2004/0106130 A1 | 6/2004 | Besemer et al. |
| 2004/0132172 A1 | 7/2004 | Cunningham et al. |
| 2004/0150829 A1 | 8/2004 | Koch et al. |
| 2004/0155309 A1* | 8/2004 | Sorin et al. ............ 257/433 |
| 2004/0166525 A1 | 8/2004 | Besemer et al. |
| 2004/0166593 A1 | 8/2004 | Nolte et al. |
| 2004/0223881 A1 | 11/2004 | Cunningham et al. |
| 2004/0229254 A1 | 11/2004 | Clair |
| 2004/0247486 A1 | 12/2004 | Tiefenthaler |
| 2004/0258927 A1 | 12/2004 | Conzone et al. |
| 2005/0002827 A1 | 1/2005 | McIntyre et al. |
| 2005/0003459 A1 | 1/2005 | Krutzik |
| 2005/0019901 A1 | 1/2005 | Matveeva et al. |
| 2005/0042628 A1 | 2/2005 | Rava et al. |
| 2005/0084422 A1 | 4/2005 | Kido et al. |
| 2005/0084895 A1 | 4/2005 | Besemer et al. |
| 2005/0106746 A1 | 5/2005 | Shinn et al. |
| 2005/0123907 A1 | 6/2005 | Rava et al. |
| 2005/0131745 A1 | 6/2005 | Keller et al. |
| 2005/0158819 A1 | 7/2005 | Besemer et al. |
| 2005/0176058 A1 | 8/2005 | Zaffaroni et al. |
| 2005/0191630 A1 | 9/2005 | Besemer et al. |
| 2005/0214950 A1 | 9/2005 | Roeder et al. |
| 2005/0226769 A1 | 10/2005 | Shiga |
| 2005/0248754 A1 | 11/2005 | Wang et al. |
| 2005/0254062 A1* | 11/2005 | Tan et al. ............ 356/480 |
| 2005/0259260 A1 | 11/2005 | Wakita |
| 2005/0272037 A1* | 12/2005 | Garey et al. ............ 435/6 |
| 2006/0040380 A1 | 2/2006 | Besemer et al. |
| 2006/0078935 A1 | 4/2006 | Werner et al. |
| 2006/0204399 A1 | 9/2006 | Freeman et al. |
| 2006/0210449 A1 | 9/2006 | Zoval et al. |
| 2006/0223172 A1 | 10/2006 | Bedingham et al. |
| 2006/0234267 A1 | 10/2006 | Besemer et al. |
| 2006/0256676 A1 | 11/2006 | Nolte et al. |
| 2006/0257939 A1 | 11/2006 | Demers |
| 2006/0269450 A1 | 11/2006 | Kim et al. |
| 2006/0270064 A1 | 11/2006 | Gordon et al. |
| 2007/0003436 A1 | 1/2007 | Nolte et al. |
| 2007/0003979 A1 | 1/2007 | Worthington |
| 2007/0070848 A1 | 3/2007 | Worthington et al. |
| 2007/0077599 A1 | 4/2007 | Krutzik |
| 2007/0077605 A1 | 4/2007 | Hurt et al. |

FOREIGN PATENT DOCUMENTS

| | | |
|---|---|---|
| EP | 1424549 | 6/2004 |
| WO | WO 9104489 | 4/1991 |
| WO | WO 9104491 | 4/1991 |
| WO | WO 9113353 | 9/1991 |
| WO | WO 9214136 | 8/1992 |
| WO | WO 9403774 | 2/1994 |
| WO | WO 9837238 | 8/1998 |
| WO | WO 0000265 | 1/2000 |
| WO | WO 0039584 | 7/2000 |
| WO | WO 0111310 | 2/2001 |
| WO | WO 0144441 | 6/2001 |
| WO | WO 2006/075797 | 7/2006 |

OTHER PUBLICATIONS

Blouin, A., et al. Detection of Ultrasonic Motion of a Scattering Surface by Two-Wave Mixing in a Photorefractive GaAs Crystal, Appl. Phys. Lett., vol. 65, pp. 932-934 (1994).

Nolte, D.D., Self-Adaptive Optical Holography in Quantum Wells, Pro. Of SPIE, vol. 37:29, pp. 237-243 (1999).

Nolte, D., et al. Photorefractive Quantum Wells (Nov. 2004).

Nagarajan, R., Intensity-based segmentation of microarrays images. IEEE Trans. Med. Imaging. v22. 882-889 (2003).

Faramarzpour, N., Shirani, S. and Bondy, J., Lossless DNA microarray image compression. IEEE Conf. Signal Systems Comput. v2. 1501-1504 (2003).

Katzer, M., Kummert, F. and Sagerer, G., Methods for automatic microarray image segmentation. IEEE Trans. NanoBiosci. v2 i4. 202-214 (2003).

N. Brändle, H. Bischof, H. Lapp: "Robust DNA Microarray Image Analysis"; Machine Vision and Applications, 15 (2003), 1; 11-28.

Nagarajan, R and Peterson, C.A. [2002] Identifying Spots in Microarray Images IEEE Trans. Nanobioscience, 1(2), 78-84.

Fabri, R: "Towards non-parametric gridding of Microarray images," Digital Signal Processing, 2002. DSP 2002. 2002 14th International Conference publication, vol. 2, pp. 623-626.

Chiao-Ling Shih, Hung-Wen Chiu, "Automatic spot detection of cDNA Microarray images using mathematical morphology methods," Conference on IEEE EMBS Asian-Pacific, Oct. 2003, pp. 70-71.

Macbeath, G. and S.L. Schreiber. 2000. "Printing proteins as microarrays for high-throughput function determination." Science 289:1760-1763.

Guemouri, L., J. Ogier, and J. J. Ramsden, "Optical properties of protein monolayers during assembly." Journal of Chemical Physics 1998. 109:3265-3268.

Ostroff, R., A. Ettinger, H. La, M. Rihanek, L. Zalman, J. Meador III, A. K. Patick, S. Worland, and B. Polisky. 2001. "Rapid multiserotype detection of human rhinoviruses on optically coated silicon surfaces." J. Clin. Virol. 21: 105-117.

Jenison, R., Yang, S., Haeberli, A., and Polisky, B., "Interference-Based Detection Of Nucleic Acid Targets On Optically Coated Silicon," Nature Biotechnology 19:62-65 (2001).

N. B. Sheller, S. Petrash, M.D. Foster, "Atomic Force Microscopy and X-ray Reflectivity Studies of Albumin Adsorbed onto Self-Assembled Monolayers of Hexadecyltrichlorosilane," Langmuir, 14, 4535-4544, 1998.

M. Varma, D. D. Nolte, H. D. Inerowicz, and F. E. Regnier, "Multi-Analyte Array Micro-Diffraction Interferometry," in *Microarrays: Design, Fabrication and Reading*, vol. 4626, B. J. B. e. al., Ed.: SPIE, 2002, pp. 69-77.

D. D. Nolte and M. R. Melloch, "Photorefractive Quantum Wells and Thin Films," in *Photorefractive Effects and Materials*, D. D. Nolte, Ed. Dordrecht: Kluwer Academic Publishers, pp. 373-451, 1995.

D. S. Gerber, R. Droopad, and G. N. Maracas, "A GaAs/AlGaAs Asymmetric Fabry-Perot Reflection Modulator with very High Contrast Ratio," *IEEE Phot. Tech. Lett.*, vol. 5, pp. 55-58, 1993.

M. Whitehead and G. Parry, "High-contrast reflection modulation at normal incidence in asymmetric multiple quantum well Fabry-Perot structure," *Electron. Lett.*, vol. 25, pp. 566-568, 1989.

B. J. Luff, J. S. Wilkinson, J. Piehler, U. Hollenbach, J. Ingenhoff, and N. Fabricius, "Integrated optical Mach-Zehnder biosensor," *Journal of Lightwave Technology*, vol. 16, pp. 583-592, 1998.

B. Drapp, J. Piehler, A. Brecht, G. Gauglitz, B. J. Luff, J. S. Wilkinson, and J. Ingenhoff, "Integrated optical Mach-Zehnder interferometers as simazine immunoprobes," *Sensors and Actuators B-Chemical*, vol. 39, pp. 277-282, 1997.

L. U. Kempen and R. E. Kunz, "Replicated Mach-Zehnder interferometers with focusing grating couplers for sensing applications," *Sensors and Actuators B-Chemical*, vol. 39, pp. 295-299, 1997.

V. S.-Y. Lin, K. Motesharei, K.-P. S. Dancil, M. Sailor, and M. R. Ghadiri, "A porous silicon-based optical interferometric biosensor," *Science*, vol. 278, pp. 840-843, 1997.

Y. C. Cao, R. Jin, and C. A. Mirkin, "Nanoparticles with Raman Spectroscopic Fingerprints for DNA and RNA Detection," *Science*, vol. 297, pp. 1536-1540, 2002.

T. A. Taton, C. A. Mirkin, and R. L. Letsinger, "Scanometric DNA Array Detection with Nanoparticle Probes," *Science*, vol. 289, pp. 1757-1760, 2000.

C. Gurtner, E. Tu, N. Jamshidi, R. W. Haigis, T. J. Onofrey, C. F. Edman, R. Sosnowski, B. Wallace, and M. J. Heller, "Microelectronic array devices and techniques for electric field enhanced DNA hybridization in low-conductance buffers," *Electrophoresis*, vol. 23, pp. 1543-1550, 2002.

Y. Joon Mo, J. Bell, H. Ying, M. Tirado, D. Thomas, A. H. Forster, R. W. Haigis, P. D. Swanson, R. B. Wallace, B. Martinsons, and M. Krihak, "An integrated, stacked microlaboratory for biological agent detection with DNA and immunoassays," *Biosensors & Bioelectronics*, vol. 17, pp. 605-618, 2002.

M. J. Heller, "An active microelectronics device for multiplex DNA analysis," *IEEE Engineering in Medicine & Biology Magazine*, vol. 15, pp. 100-104, 1996.

D. D. Nolte and K. M. Kwolek, "Diffraction from a Short-Cavity Fabry-Perot: Applications to Photorefractive Quantum Wells," *Opt. Commun.*, vol. 115, pp. 606-616, 1995.

R.-H. Yan, R. J. Simes, and L. A. Coldren, "Analysis and design of surface-normal Fabry-Perot electrooptic modulators," *IEEE Quant. Electron.*, vol. 25, pp. 2272-2280, 1989.

J. F. Heffernan, M. H. Moloney, J. Hegarty, J. S. Roberts, and M. Whitehead, "All optical high contrast absorptive modulation in an asymmetric Fabry-Perot etalon," *Appl. Phys. Lett.*, vol. 58, pp. 2877-2879, 1991.

A. Larsson and J. Maserjian, "Optically addressed asymmetric Fabry-Perot modulator," *Appl. Phys. Lett.*, vol. 59, pp. 3099-3101, 1991.

K. M. Kwolek, M. R. Melloch, and D. D. Nolte, "Dynamic holography in a reflection/transmission photorefractive quantum-well asymmetric Fabry-Perot," *Appl. Phys. Lett.*, vol. 65, pp. 385-387, 1994.

D. D. Nolte, "Dynamic Holographic Phase Gratings in Multiple Quantum Well Asymmetric Reflection Fabry-Perot Modulators," *Opt. Lett.*, vol. 19, pp. 819-821, 1994.

Kwolek, K.M. et al, "Photorefractive Asymmetric Fabry-Perot Quantum Wells: Transverse-filed Geometry," Appl. Phys. Lett, vol. 67, pp. 736-738, 1995.

B. A. Grzybowski, R. Haag, N. Bowden, and G. M. Whitesides, "Generation of micrometer-sized patterns for microanalytical applications using a laser direct-write method and microcontact printing," *Anal. Chem.*, vol. 70, pp. 4645-4652, 1998.

T. Cass and F. S. Ligler, "Immobilized Biomolecules in Analysis: A Practical Approach Series vol. 98," Oxford: Oxford, 1998.; Chapter 2: Avidin-biotin immobilization systems, pp. 15-34.

R. Guersen, I. Lahiri, M. R. Melloch, J. M. Woodall and D. D. Nolte, Transient Enhanced Intermixing of Arsenic-Rich Nonstoichiometric AlAs/GaAs Quantum Wells, Phys. Rev. B60,10926-10934 (1999).

D. Crouse, D. D. Nolte, J. C. P. Chang, and M. R. Melloch, "Optical absorption by Ag precipitates in AlGaAs," *J. Appl. Phys.*, vol. 81, pp. 7981-7987, 1997.

G. A. Sefler, E. Oh, R. S. Rana, I. Miotkowski, A. K. Ramdas, and D. D. Nolte, "Faraday Photorefractive Effect in a Diluted Magnetic Semiconductor," *Opt. Lett.*, vol. 17, pp. 1420-1422, 1992.

J. M. McKenna, D. D. Nolte, W. Walukiewicz, and P. Becla, "Persistent holographic absorption gratings in AlSb:Se," *Appl. Phys. Lett.*, vol. 68, pp. 735-737, 1996.

R. S. Rana, E. Oh, K. Chua, A. K. Ramdas, and D. D. Nolte, "Voigtphotorefractive two-wave mixing in CdMnTe," *J. Lumin.*, vol. 60&61, pp. 56-59, 1994.

L. Peng, P. Yu, D. D. Nolte, and M. R. Melloch, "High-speed adaptive interferometer for optical coherence-domain reflectometry through turbid media," Opt. Lett. 28, 396-398 (2003).

R. M. Brubaker, Y. Ding, D. D. Nolte, M. R. Melloch, and A. M. Weiner, "Bandwidth-Limited Diffraction of Femtosecond Pulses from Photorefractive Quantum Wells," *IEEE J. Quant. Electron.*, vol. 33, pp. 2150-2158, 1997.

Y. Ding, D. D. Nolte, M. R. Melloch, and A. M. Weiner, "Real-time edge enhancement of femtosecond time-domain images by use of photorefractive quantum wells," *Opt. Lett.*, vol. 22, pp. 1101-1103, 1997.

Y. Ding, D. D. Nolte, M. R. Melloch, and A. M. Weiner, "Time-domain image processing using dynamic holography," *IEEE J. Sel. Top. Quant. Elect.*, vol. 4, pp. 332-341, 1998.

M. Dinu, D. D. Nolte, and M. R. Melloch, "Electroabsorption spectroscopy of effective-mass AlGaAs/GaAs Fibonacci superlattices," *Phys. Rev. B*, vol. 56, pp. 1987-1995, 1997.

M. Dinu, K. Nakagawa, M. R. Melloch, A. M. Weiner, and D. D. Nolte, "Broadband Low-Dispersion Diffraction of Femtosecond Pulses from Photorefractive Quantum Wells," *J. Opt. Soc. Am. B*, vol. 17, pp. 1313-1319, 2000.

Y. Ding, D. D. Nolte, Z. Zheng, A. Kanan, A. M. Weiner, and G. A. Brost, "Bandwdith Study of Volume Holography in Photorefrative InP:Fe at 1.5 microns for Frequency Domain Femtosecond Pulse Processing," *J. Opt. Soc. B*, vol. 15, pp. 2763-2768, 1998.

Y. Ding, I. Lahiri, D. D. Nolte, G. J. Dunning, and D. M. Pepper, "Electric Field Correlation of Femtosecond Pulses Using a Photo-Electromotive Force Detector," *J. Opt. Soc. Am. B*, vol. 15, pp. 2013-2017, 1998.

R. Jones, N. P. Barry, S. C. W. Hyde, P. M. W. French, K. M. Kwolek, D. D. Nolte, and M. R. Melloch, "Direct-to-Video holographic readout in quantum wells for 3-D imaging through turbid media," *Opt. Lett.*, vol. 23, pp. 103-105, 1998.

R. Jones, M. Tziraki, P. M. W. French, K. M. Kwolek, D. D. Nolte, and M. R. Melloch, "Direct-to-video holographic 3-D imaging using photorefractive multiple quantum well devices," *Optics Express*, vol. 2, pp. 439-448, 1998.

M. Tziraki, R. Jones, P. M. W. French, M. R. Melloch, and D. D. Nolte, "Photorefractive Holography for Imaging through turbid media using low coherence light," *Appl. Phys. B*, vol. 70, pp. 151-154, 1999.

M. Tziraki, R. Jones, P. French, D. Nolte, and M. Melloch, "Short-coherence photorefractive holography in multiple-quantum-well devices using light-emitting diodes," *Appl. Phys. Lett.*, vol. 75, pp. 363-365, 1999.

I. Lahiri, D. D. Nolte, M. R. Melloch, and M. B. Klein, "Oscillatory mode coupling and electrically strobed gratings in photorefractive quantum-well diodes," *Optics Lett.*, vol. 23, pp. 49-51, 1998.

I. Lahiri, L. J. Pyrak-Nolte, D. D. Nolte, and M. R. Melloch, "Transient Dynamics During Two-Wave Mixing in Photorefractive Quantum Well Diodes using Moving Gratings," *Opt. Express*, vol. 2, pp. 432-438, 1998.

C.-C. Wang, R. A. Linke, D. D. Nolte, M. R. Melloch, and S. Trivedi, "Enhanced detection bandwidth for optical doppler frequency measurements using moving space charge field effects in GaAs multiple quantum wells," *Appl. Phys. Lett.*, vol. 70, pp. 2034-2036, 1997.

C. C. Wang, R. A. Linke, D. D. Nolte, M. R. Melloch, and S. Trivedi, "Signal strength enhancement and bandwidth tuning in moving space charge field photodetectors using alternating bias field," *Appl. Phys. Lett.*, vol. 72, pp. 100-102, 1998.

D. M. Pepper, G. J. Dunning, M. P. Chiao, T. R. O'Meara, P. V. Mitchell, I. Lahiri, and D. D. Nolte, "Characterization of the photo-EMF response for laser-based ultrasonic sensing under simulated industrial conditions," *Rev. Prog. Quant. Nondestruct. Eval.*, vol. 17, pp. 627-634, 1998.

D. D. Nolte, *Mesoscopic Pointlike Defects in Semiconductors: Deep-level Energies*, Phys. Rev. B 58, 7994-8001 (1998).

M. Dinu, I. Miotkowski, and D. D. Nolte, *Magnetic Quenching of Time-Reversed Light in Photorefractive Diluted Magnetic Semiconductors*, Phys. Rev. B 58, 10435 (1998).

S. Balasubramanian, S. W. Mansour, M. R. Melloch and D. D. Nolte, *Vacancy diffusion Kinetics in arsenic-rich nonstoichiometric AlAs/GaAs heterostructures*, Phys. Rev. B 63, 033305-1-033305-3 (2000).

David D. Nolte, Manoj M. Varma, Leilei Peng, Halina D. Inerowicz, Fred E. Regnier, *Spinning-disk laser interferometers for immunoassays and proteomics: the BioCD* in Proc. SPIE vol. 5328,, Microarrays and Combinatorial Techniques: Design, Fabrication, and Analysis II; Dan V. Nicolau, Ramesh Raghavachari; Eds., p. 41-48 (2004).
Manoj M. Varma, Halina D. Inerowicz, Fred E. Regnier, David D. Nolte, *Real-time spinning-disk interferometric immunoassays*, in Proc. SPIE vol. 5328, Microarrays and Combinatorial Techniques: Design, Fabrication, and Analysis II; Dan V. Nicolau, Ramesh Raghavachari; Eds., p. 62-68 (2004).
T. Jensen, L. Kelly, A. Lazarides, and G. C. Schatz, "Electrodynamics of noble metal nanoparticles and nanoparticle clusters," *Journal of Cluster Science*, vol. 10, pp. 295-317, 1999.
H. Kuwata, H. Tamaru, K. Esumi, and K. Miyano, "Resonant light scattering from metal nanoparticles: Practical analysis beyond Rayleigh approximation," *Applied Physics Letters*, vol. 83, pp. 4625-4627, 2003.
M.J. Jory, P. S. Cann, J. R. Sambles, and E. A. Perkins, "Surface-plasmon-enhanced light scattering from microscopic spheres," *Applied Physics Letters*, vol. 83, pp. 3006-3008, 2003.
K.L. Kelly, E. Coronado, L. L. Zhao, and G. C. Schatz, "The optical properties of metal nanoparticles: The influence of size, shape, and dielectric environment," *Journal of Physical Chemistry B*, vol. 107, pp. 668-677, 2003.
P. Chakraborty, "Metal nanoclusters in glasses as non-linear photonic materials," *Journal of Materials Science*, vol. 33, pp. 2235-2249, 1998.
S. J. Oldenburg, S. L. Westcott, R. D. Averitt, and N. J. Halas, "Surface enhanced Raman scattering in the near infrared using metal nanoshell substrates," *Journal of Chemical Physics*, vol. 111, pp. 4729-4735, 1999.
P. Mulvaney, "Surface plasmon spectroscopy of nanosized metal particles," *Langmuir*, vol. 12, pp. 788-800. 1996.
H.F. Ghaemi, T. Thio, D. E. Grupp, T. W. Ebbesen, and H. J. Lezec, "Surface plasmons enhance optical transmission through subwavelength holes," *Physical Review B*, vol. 58, pp. 6779-6782, 1998.
M. Minunni and M. Mascini, "Detection of Pesticide in Drinking-Water Using Real-Time Biospecific Interaction Analysis (Bia)," *Analytical Letters*, vol. 26, pp. 1441-1460, 1993.
C. Mouvet, R. D. Harris, C. Maciag, B. J. Luff, J. S. Wilkinson, J. Piehler, A. Brecht, G. Gauglitz, R. Abuknesha, and G. Ismail, "Determination of simazine in water samples by waveguide surface plasmon resonance," Analytica Chimica Acta, vol. 338, pp. 109-117, 1997.
A. Rasooly, "Surface plasmon resonance analysis of staphylococcal enterotoxin B in food," *Journal of Food Protection*, vol. 64, pp. 37-43, 2001.
G. Sakai, K. Ogata, T. Uda, N. Miura, and N. Yamazoe, "A surface plasmon resonance-based immunosensor for highly sensitive detection of morphine," Sensors and Actuators B-Chemical, vol. 49, pp. 5-12, 1998.
G. Sakai, S. Nakata, T. Uda, N. Miura, and N. Yamazoe, "Highly selective and sensitive SPR immunosensor for detection of methamphetamine," Electrochimica Acta, vol. 44, pp. 3849-3854, 1999.
E. Kretschmann and H. Raether, "Radiative Decay of Non Radiative Surface Plasmons Excited by Light," *Zeitschrift Fur Naturforschung Part a-Astrophysik Physik Und Physikalische Chemie*, vol. A 23, pp. 2135-2136, 1968.
A. Otto, "Excitation of Nonradiative Surface Plasma Waves in Silver by Method of Frustrated Total Reflection," *Zeitschrift Fur Physik*, vol. 216, pp. 398-410, 1968.
J. Homola, S. S. Yee, and G. Gauglitz, "Surface plasmon resonance sensors: review," Sensors and Actuators B-Chemical, vol. 54, pp. 3-15, 1999.
M. Malmqvist, "BIAcore: an affinity biosensor system for characterization of biomolecular interactions," *Biochemical Society Transactions*, vol. 27, 1999.
M. Fivash, E. M. Towler, and R. J. Fisher, "BIAcore for macromolecular interaction," Current Opinion in Biotechnology, vol. 9, pp. 97-101, 1998.
L.D. Roden and D. G. Myszka, "Global analysis of a macromolecular interaction measured on BIAcore," Biochemical and Biophysical Research Communications, vol. 225, pp. 1073-1077, 1996.

C.F. R. Mateus, M. C. Y. Huang, B. T. Cunningham, and C. J. Chang-Hasnain, "Compact label-free biosensor using VCSEL-based measurement system," Ieee Photonics Technology Letters, vol. 16, pp. 1712-1714, 2004.
P. Y. Li, L. Bo, J. Gerstenmaier, and B. T. Cunningham, "A new method for label-free imaging of biomolecular interactions," Sensors and Actuators B-Chemical, vol. 99, pp. 6-13, 2004.
G. Walter, K. Bussow, A. Lueking, and J. Glokler, "High-throughput protein arrays: prospects for molecular diagnostics," Trends in Molecular Medicine, vol. 8, pp. 250-253, 2002.
J.B. Pendry, L. Martin-Moreno, and F. J. Garcia-Vidal, "Mimicking surface plasmons with structured surfaces," Science, vol. 305, pp. 847-848, 2004.
A.G. Brolo, R. Gordon, B. Leathem, and K. L. Kavanagh, "Surface plasmon sensor based on the enhanced light transmission through arrays of nanoholes in gold films," Langmuir, vol. 20, pp. 4813-4815, 2004.
J. A. Coy, D. D. Nolte, G. J. Dunning, D. M. Pepper, B. Pouet, G. D. Bacher, and M. B. Klein, "Asymmetric Interdigitated MSM Contacts for Improved Adaptive Photo-EMF Detectors," J. Opt. Soc. Am. B, vol. 17, pp. 697-704, 1999.
J. Coy, F. Stedt, I. Lahiri, M. Melloch, and D. Nolte, "Exciton electroabsorption moments and sum rules," Opt. Commun., vol. 176, pp. 17-29, 2000.
R. S. Rana, E. Oh, K. Chua, A. K. Ramdas, and D. D. Nolte, "Magneto-photorefractive effects in a diluted magnetic semiconductor," *Phys. Rev. B*, vol. 49, pp. 7941-7951, 1994.
D. D. Nolte, I. Lahiri, J. McKenna, F. R. Steldt, J. C. P. Chang, M. R. Melloch, and J. M. Woodall, "Wannier excitons in a Coulomb Cage," presented at 23rd Int. Conf. Phys. Semicond., Vancouver, Canada, 1994.
D. D. Nolte, J. A. Coy, G. J. Dunning, D. M. Pepper, M. P. Chiao, G. D. Bacher, and M. B. Klein, "Enhanced responsivity of non-steady-state photoinduced electromotive force sensors using asymmetric interdigitated contacts," Opt. Lett., vol. 24, pp. 342-344, 1999.
D. M. Pepper, G. J. Dunning, D. D. Nolte, J. Coy, M. B. Klein, G. D. Bacher, and B. Pouet, "Enhanced Responsivity of Photo-Induced-emf Laser Ultrasound Sensors Using Asymmetric Interdigitated Contacts," in Review of Progress in Quantitative Nondestructive Evaluation, vol. 19, D. O. Thompson and D. E. Chimenti, Eds. New York: American Institute of Physics Press, 2000, pp. 2013-2020.
Technology paper entitled "Grating-Coupled Surface Plasmon Resonance (GCSPR)"—printed from HTS Biosystems Technologies website (www.htsbiosystems.com/technology/gcspr.htm) on May 2, 2005.
B. Cunningham, P. Li, and J. Pepper, "Colorimetric resonant reflection as a direct biochemical assay technique," Sensors and Actuators B, vol. 81, pp. 316-328, 2002.
Polizzi, M.A., Plocinik, R.M., and Simpson, G.J., "Ellipsometric Approach for the Real-Time Detection of Label-Free Protein Adsorption by Second Harmonic Generation," J. Am. Chem. Soc., 126, 15, 5001-5007, 2004.
Plocinik, R. M.; Simpson, G. J., Polarization characterization in surface second harmonic generation by nonlinear optical null ellipsometry. Analytica Chimica Acta 2003, 496, (1-2), 133-142.
P. B. Luppa, L. J. Sokoll, and D. W. Chan, "Immunosensors—principles and applications to clinical chemistry," *Clinica Chimica Acta*, vol. 314, pp. 1-26, 2001.
C. L. Tucker, J. F. Gera, and P. Uetz, "Towards an understanding of complex protein networks," *Trends In Cell Biology*, vol. 11, pp. 102-106, 2001.
P. Uetz and R. L. Finley, "From protein networks to biological systems," *Febs Letters*, vol. 579, pp. 1821-1827, 2005.
G. Gauglitz, "Direct optical sensors: principles and selected applications," Analytical And Bioanalytical Chemistry, vol. 381, pp. 141-155, 2005.
S. P. Balk, Y.-J. Ko, and G. J. Bubley, "Biology of Prostate-specific antigen," J. Clin. Onc., vol. 21, pp. 383-391, 2003.
Wang, M.C., Papsidero, L.D., Kuriyama, M., Valenzuela, G.P. and Chu, T.M. 1981. Prostate antigen: A new potential marker for prostatic cancer. The Prostate 2: 89-96.
Musundi et al., "Approaching Real-Time Molecular Diagnostics: Single-Pair Fluorescence Resonance Energy Transfer (spFRET)

Detection for the Analysis of Low Abundant Point Mutations in K-ras Oncogenes," J Am Chem Soc. Jun. 11, 2003;125(23):6937-45.

Lovgren J, Valtonen-Andre C, Marsal K, et al: Measurement of prostate-specific antigen and human glandular kallikrein 2 in different body fluids. J. Androl. 20:348-355, 1999.

J. Homola, "Present and future of surface plasmon resonance biosensors," Analytical And Bioanalytical Chemistry, vol. 377, pp. 528-539, 2003.

Konstantinos Blekas, Nikolas P. Galatsanos, Aristidis Likas, Isaac E. Lagaris: Mixture model analysis of DNA microarray images. IEEE Trans. Med. Imaging 24(7): 901-909 (2005).

Peter Bajcsy: Gridline: automatic grid alignment DNA microarray scans. IEEE Transactions on Image Processing 13(1): 15-25 (2004).

T.W. Ebbesen, H. J. Lezec, H. F. Ghaemi, T. Thio, and P. A. Wolff, "Extraordinary optical transmission through sub-wavelength hole arrays," *Nature*, vol. 391, pp. 667-669, 1998.

D.A. Genov, A. K. Sarychev, V. M. Shalaev, and A. Wei, "Resonant field enhancements from metal nanoparticle arrays," *Nano Letters*, vol. 4, pp. 153-158, 2004.

V. Koubova, E. Brynda, L. Karasova, J. Skvor, J. Homola, J. Dostalek, P. Tobiska, and J. Rosicky, "Detection of foodborne pathogens using surface plasmon resonance biosensors," Sensors and Actuators B-Chemical, vol. 74, pp. 100-105, 2001.

Xia, Y, et al. Non Photolithographic Methods and Fabrication of Elastomeric Stamps for Use in Microcontact Printing, Langmuir, 1996, vol. 12, pp. 4033-4038.

Hu, J., et al. Using Soft Lithography to Fabricate GaAs/AlGaAs Hetreostructue Field Effect Transistors, Appl. Phys.Lett., 1997 vol. 71, pp. 2020-2002.

Grzybowski, B.A., et al. Generation of Micrometer-Sized Patterns For Microanalytical Applications Using a Laser Direct-Write Method and Microcontact Printing, Anal. Chem., 1998, vol. 70, p. 4645-4652.

Martin, B.D., et al., Direct Protein Microarray Fabrication Using a Hydrogel Stamper, Langmuir, 1998, vol. 14, pp. 3971-3975.

Pompe, T., et al., Submicron Contact Printing On Silicon Using Stamp Pads, Langmuir, 1999, vol. 15, pp. 2398-2401.

Bietsch, A. and B. Michel, Conformal Contact And Pattern Stability of Stamps Used For Soft Lithography, J. Appl. Phys., 2000, vol. 88, pp. 4310-4318.

Geissler, M., et al., Mictrocontact Printing Chemical Patterns With Flat Stamps, J. Am. Chem. Soc., 2000, vol. 122, pp. 6303-6304.

Sanders, G.H.W. and A. Manz, Chip-based Microsystems For Genomic and Proteomic Analysis. Trends in Anal, Chem., 2000, vol. 19(6), pp. 3465-3478.

Wang, J., Survey and Summary From DNA Biosensors To Gene Chips, Nucl. Acids Res., 2000 vol. 28(16), pp. 3011-3016.

Hagman, M., Doging Immunology On a Chip, Science, 2000, vol. 290, pp. 82-83.

Marx, J., DNA Arrays Reveal Cancer In Its Many Forms, Science, 2000, vol. 289, pp. 1670-1672.

Effenhauser, C.S., et al. Integrated Capillary Electrophoresis On Flexible Silicone Microdevices: Analysis of DNA Restriction Fragments and Detection Of Single DNA Molecules On Microchips. Anal. Chem., 1997, vol. 69, pp. 3451-3457.

He, B. and F.E.. Regnier, Fabrication of Nanocolumns for Liquid Chromatography, Anal. Chem., 1998, vol. 70, p. 3790-3797.

Kricka, L.J., Miniaturization of Analytical Systems. Clin. Chem., 1998, vol. 44(9), pp. 2008-2014.

Regnier, F.E., et al. Chromatography and Electrophoresis On Chips: Critical Elements Offuture Integrated, Microfluidic Analytical Systems For Life Science. Tibtdch, 1999, vol. 17, pp. 101-106.

Ekins, R.,F. Chu, and E. Biggart, Development of Microspot Multi-Analyte Ratiometric Immunoassay Using Dual Flourescent-Labelled Antibodies. Anal. Chim. Acta, 1989, vol. 227, pp. 73-96.

Gao, H., et al., Immunosensing With Photo-Immobilized Immunoreagents On Planar Optical Wave Guides. Biosensors and Bioelecctronics, 1995, vol. 10, pp. 317-328.

Maisenholder, B., et al. A GaAs/AlGaAs-based Refractometer Platform For Integrated Optical Sensing Applications. Sensors and Actuators B, 1997, vol. 38-39, pp. 324-329.

Kunz, R.E., Miniature Integrated Optical Modules For Chemical and Biochemical Sensing. Sensors and Actuators B, 1997, vol. 38-39, pp. 13-28.

DuBendorfer, J. and R.E. Kunz, Reference Pads For Miniaure Integrated Optical Sensors. Sensors and Actuatores B, 1997 vol. 38-39, pp. 1-7.

Hecht, E., Optics, 1987: Addison-Wesely publishing Co., Inc.

Scruby, C.B. and L.E. Drain, Laser Ultrasonics: Techniques and Applications. 1990, Bristol: Adam Hilger.

Nolte, D.D. , et al., Adaptive Beam Combining and Interferometry Using Photorefractive Quantum Wells, J. Opt. Soc. Am. B, vol. 19, No. 2, Feb. 2001, pp. 195-205.

St. John et al., "Diffraction-Based Cell Detection Using a Microcontact Printed Antibody Grating", Analytical Chemistry, 1998, vol. 70, No. 6, pp. 1108-1111.

Morhard, F., et al., Immobilization Of Antibodies In Micropatterns For Cell Detection By Optical Diffraction. Sensors and Actuators B, 2000, vol. 70, pp. 232-242.

I. Rossomakhin and. Stepanov, Linear Adaptive Interferometers Via Diffusion Recording In Cubic Photorefractive Crystals, Opt. Commun. 86, 199-204 (1991).

Ing R.K and Monchalin, L.P. , Broadband Optical Detection of Ultrasound By Two-Wave Mixing In a Photorefractive Crystal, Appl. Phys. Lett. 59, 3233-5 (1991).

Delaye, P. et al., Detection of Ultraonic Motion of a Scattering Surface by Two-Wave Mixing In a Photorefractive GaAs Crystal, Appl. Phys. Litt. 65, 932-4 (1994).

Pouet, B.F. Ing, R.K., Krishnaswanry, S, and Royer, D, Heterodyne Interferometer With Two-Wave Mixing In Photorefractive Crystals For Ultrasound Detection On Rough Surface, Appl. Phys. Lett. 69, 3782 (1996).

Montmorillon, L.A. Biaggio, I Delaye, P, Launay, J.-C., and Roosen, A, Eye Safe Large Field of View Homodyne Detection Using a Photorefractive CdTe: V Crystal, Opt. Commun. 29, 293 (1996).

P. Delaye, A. Blouin, D. Drolet, L.-A. Montmorrillong. Roosen,and J.-P. Monchalin, Detection of Ultrasonice Motion of a Scattering Surface by Photorefractive InP:Fe Under An Applied dc Field, J. Opt. Soc. Am. B14, 1723-34 (1997).

I. Lahiri, L.J. Pyrak-Nolte, D.D. Nolte, M.R. Melloch, R.A. Kruger, G.D. Backer, and M. B. Klein, Laser-Based Ultrasound Detection Using Photorefractive Uantum Wells, Appl. Phys. Lett. 73, 1041-43 (1998).

S. Balassubramanian, L.Lahiri, Y. Ding, M.R. Melloch, and D.D. Nolte, Two-Wave Mixing Dynamics and Nonlinear Hot-Electron Transport In Transverse-Geometry Photorefractive Quantum Wells Studies By Moving Grantings, Appl. Phys. B. 68, 863-9 (1990).

E. Delmarche, A. Bernard, II. Schmid, B. Michel, and H. Biebuyck, Patterned Delivery of Immonglobulines to Surface Using Microfluidic Networks, Science 276, 779-781(1997).

E. Delamarche, A. Bernard, H. Schmid, A. Bietsch, 13 Michel , and H. Biebuyck, Microfluidic Networks For Chemical Patterning of Substrates: Design and Application to Bioassays, Journal of the American Chemical Society 120, 500-508 (1998).

Kapur, Ravi et al. Streamlining the Drug Discovery Process by Integrating Miniaturization High Throughput Screening, High Content Screening, and Automation on the CellChip TM System. Biomedical Microdevices, vol. 1, No. 2, 1999, pp. 99-109.

Ekins R. et al. Multianalyte Microspot Immunoassay. The Microanalytical Compact Disk Of the Future: Clin. Chem., 1991, vol. 37(11), p. 1955-1967.

Jenison, R., Yan, S. Haeberli, A. Polisky, B., 2001. Interference-Based Detection of Nucleic Acid Targets On Optically Coated Silicon. Nat. Biotechnol. 19, pp. 62-65.

Fattinger, C., Koller, H., Schlatter, D., Wehrli, P., 1993, The Difference Interferometer—A High Sensitive Opitcal Probel For Quantification Of Molecular-Surface Concentration; Biosens, Bioelectron 8, pp. 99-107.

Jenison, Robert et al. Silicon-based Biosensors for Rapid Detection of Protein or Nucleic Acid Targets, Clinical Chemistry, 47:10, 2001 pp. 1894-1990.

Varma., M.M., et al.; High Speed Lable Free Detection By Spinning-Disk Micro-Interferometry; Biosensors & Bioelectronics, vol. 19, pp. 1371-1376, 2004.

Varma, M.M, et al.; Spinning-Disk Self-Referencing Interferrometry of Antigen-Antibody Recognition; Optics Letters, vol. 29, pp. 950-952, 2004.

Morhard et al.; Immobilization of Antibodies in Micropatterns for Cell Detection by Optical Diffraction, Sensors and Actuators B., 2000, vol. 70, pp. 232-242.

Nolte, D.D.; Semi-Insulating Semiconductor Heterostructures: Optoelectronic Properties And Applications, J.Appl.Phys. vol. 85, pp. 6269, 1999.

Brecht, A. and G. Gauglitz; Recent Developements in Optical Transducers for Chemical of Biochemical Applications. Sensors and Actuators B, 1997 vol. 38-39, pp. 1-7.

Varma, M.M. et al.; High-Speed Label-Free Multi-Analyte Detection Through Micro-Interferometry; Proc. of SPIE, vol. 496, pp. 58-64, 2003.

Ekins, R., Ligand, Assays; From Electrophoresis to Miniaturized Microaarays, Clin. Chem, 1998, vol. 44(9), pp. 2015-2030.

Somekh, Michael et al.; Scanning Heterodyne Confocal Differential Phase And Intensity Microscope, Applied Optics, vol. 34, No. 22, pp. 4857-4868; 1995.

Suddendorf, Manfred, et al.; Single-Probe-Beam Differential Amplitude And Phase-Scanning Interferometer; vol. 36, No. 25, pp. 6202-6210, 1997.

See, C.W. et al.; Scanning Differential Optical Profilometer For Simultaneous Measurement Of Amplitude and Phase Variation, Appl. Phys. Lett, vol. 53, No. 1, pp. 10-12, 1988.

Abe, Takao, et al.; Microroughness Measurements on Polished Silicon Wafers, Jpn. J. Appl. Phys., vol. 31, pp. 721-728, 1992.

Nolte, D.D. et al.; Spinning-Disk Interferometry the BioCD; Optics & Photonics News, pp. 48-53, 2004.

Ding, Y., et al.; Femtosecnd Pulse Shaping By Dynamic Holograms In Photorefractive Multiple Quantum Wells; Optical Society of America, pp. 718-720; 1997.

Ding, Y., et al., Adaptive All-Order Dispersion Compensation Of Ultrafast Laser Pulses Using Dynamic Spectral Holography; American Institute of Physics, pp. 3255-3257; 1999.

Jones, R. et al.; Adaptive Femtosecond Optical Pulse Combining; American Institute of Physics, pp. 3692-3694; 2000.

Lahiri, I et al.; Photorefractice p-i-n Diode AQuantum Well Spatial Light Modulators; American Institute of Physics, pp. 1408-738; 1995.

Nolte, D.D., Self-Adaptive Optical Hologrphy In Quantum Wells, pp. 1-6, 2005.

La Clair, J. et al.; Molecular Screening On a Compact Disc; The Royal Society of Chemistry; pp. 3244-3249; 2003.

Burkart, et al. UCSD Scientists Develope Novel Way to Screen Molecules Using Conventional CDS an Compact Disk Players; UCSD newsletter; pp. 1-4, 2003.

Kwolek, K.M. et al.; Photorefractive Asymmetric Fabry-Perot Quantum Wells: Transverse-filed Geometry; Appl. Phys. Lett, vol. 67, pp. 736-738, 1995.

Nolte, D, et al., Photorefractive Quantum Wells, 2005.

Peng, Leilei et al., Adaptive Optical biocompact Disk For Moecular Recognition, Applied Physics Letters 86, 2005.

Gruska, B, et al., Fast and Reliable Thickness and Refractive Index Measurement of Antireflection Coatings On Solar-Silicon By Eliipsometry, Sentech Instruments GmbH, Carl0Scheele-Str. 16, 12489 Berlin Germany, 2006.

* cited by examiner

MULTIPLEXED BIOLOGICAL ANALYZER PLANAR ARRAY APPARATUS AND METHODS

CROSS REFERENCE

This application claims the benefit of U.S. Provisional Patent Application Ser. No. 60/649,043, entitled "MULTIPLEXED LASER SCANNING INTERFEROMETRIC BIOCHIPS AND BIODISKS," filed on Feb. 1, 2005 and the same is expressly incorporated herein by reference.

TECHNICAL FIELD

The present invention generally relates to a device for detecting the presence of specific biological material in a sample, and more particularly to a laser compact disc system for detecting the presence of biological pathogens and/or analyte molecules bound to target receptors on the disc by sensing changes in the optical characteristics of a probe beam reflected from the disc caused by the pathogens and/or analytes.

BACKGROUND

In many chemical, biological, medical, and diagnostic applications, it is desirable to detect the presence of specific molecular structures in a sample. Many molecular structures such as cells, viruses, bacteria, toxins, peptides, DNA fragments, and antibodies are recognized by particular receptors. Biochemical technologies including gene chips, immunological chips, and DNA arrays for detecting gene expression patterns in cancer cells, exploit the interaction between these molecular structures and the receptors. [For examples see the descriptions in the following articles: Sanders, G. H. W. and A. Manz, *Chip-based microsystems for genomic and proteomic analysis*. Trends in Anal. Chem., 2000, Vol. 19(6), p. 364-378. Wang, J., *From DNA biosensors to gene chips*. Nucl. Acids Res., 2000, Vol. 28(16), p. 3011-3016; Hagman, M., *Doing immunology on a chip*. Science, 2000, Vol. 290, p. 82-83; Marx, J., *DNA Arrays reveal cancer in its many forms*. Science, 2000, Vol. 289, p. 1670-1672]. These technologies generally employ a stationary chip prepared to include the desired receptors (those which interact with the target analyte or molecular structure under test). Since the receptor areas can be quite small, chips may be produced which test for a plurality of analytes. Ideally, many thousand binding receptors are provided to provide a complete assay. When the receptors are exposed to a biological sample, only a few may bind a specific protein or pathogen. Ideally, these receptor sites are identified in as short a time as possible.

One such technology for screening for a plurality of molecular structures is the so-called immunological compact disk, which simply includes an antibody microarray. [For examples see the descriptions in the following articles: Ekins, R., F. Chu, and E. Biggart, *Development of microspot multi-analyte ratiometric immunoassay using dual flourescent-labelled antibodies*. Anal. Chim. Acta, 1989, Vol. 227, p. 73-96; Ekins, R. and F. W. Chu, *Multianalyte microspot immunoassay—Microanalytical "compact Disk" of the future*. Clin. Chem., 1991, Vol. 37(11), p. 1955-1967; Ekins, R., *Ligand assays: from electrophoresis to miniaturized microarrays*. Clin. Chem., 1998, Vol. 44(9), p. 2015-2030]. Conventional fluorescence detection is employed to sense the presence in the microarray of the molecular structures under test. Other approaches to immunological assays employ traditional Mach-Zender interferometers that include waveguides and grating couplers. [For examples see the descriptions in the following articles: Gao, H., et al., *Immunosensing with photo-immobilized immunoreagents on planar optical wave guides*. Biosensors and Bioelectronics, 1995, Vol. 10, p. 317-328; Maisenholder, B., et al., *A GaAs/AlGaAs-based refractometer platform for integrated optical sensing applications*. Sensors and Actuators B, 1997, Vol. 38-39, p. 324-329; Kunz, R. E., *Miniature integrated optical modules for chemical and biochemical sensing*. Sensors and Actuators B, 1997, Vol. 38-39, p. 13-28; Dübendorfer, J. and R. E. Kunz, *Reference pads for miniature integrated optical sensors*. Sensors and Actuators B, 1997 Vol. 38-39, p. 116-121; Brecht, A. and G. Gauglitz, *recent developments in optical transducers for chemical or biochemical applications*. Sensors and Actuators B, 1997, Vol. 38-39, p. 1-7].

While the abovementioned techniques have proven useful for producing and reading assay information within the chemical, biological, medical and diagnostic application industries, developing improved fabrication and reading techniques for planar arrays with significant improvement in performance over existing planar array technology is desirable.

SUMMARY

One embodiment according to the present invention includes a planar array having plurality of biological recognition molecules including at least two types of biological recognition molecules distributed about a substrate. A first type of biological recognition molecules is distributed according to a first frequency and a second type of biological recognition molecules is distributed according to a second frequency.

Another embodiment according to the present invention includes a planar array having plurality of biological recognition molecules including at least two kinds of biological recognition molecules distributed about a substrate. A first kind of biological recognition molecules is distributed at a first height or depth relative to a surface of the substrate and a second kind of biological recognition molecules is distributed at a second height or depth relative to the surface.

A further embodiment according to the present invention includes an apparatus including a surface normal interferometry platform including a scanning pathway and a plurality of analyzer molecules adapted to detect the presence or absence of a plurality of target analytes. The plurality of analyzer molecules are distributed about the scanning pathway according to a multiplexing scheme.

Another embodiment of the present invention includes a method including multiplexing a plurality of kinds of capture molecules about a detection pathway, contacting a biological sample to the array, detecting the presence or absence of binding of the plurality of kinds of capture molecules and a plurality of target analytes using interferometry.

Additional embodiments, aspects, and advantages of the present invention will be apparent from the following description.

DETAILED DESCRIPTION

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Figure 1:
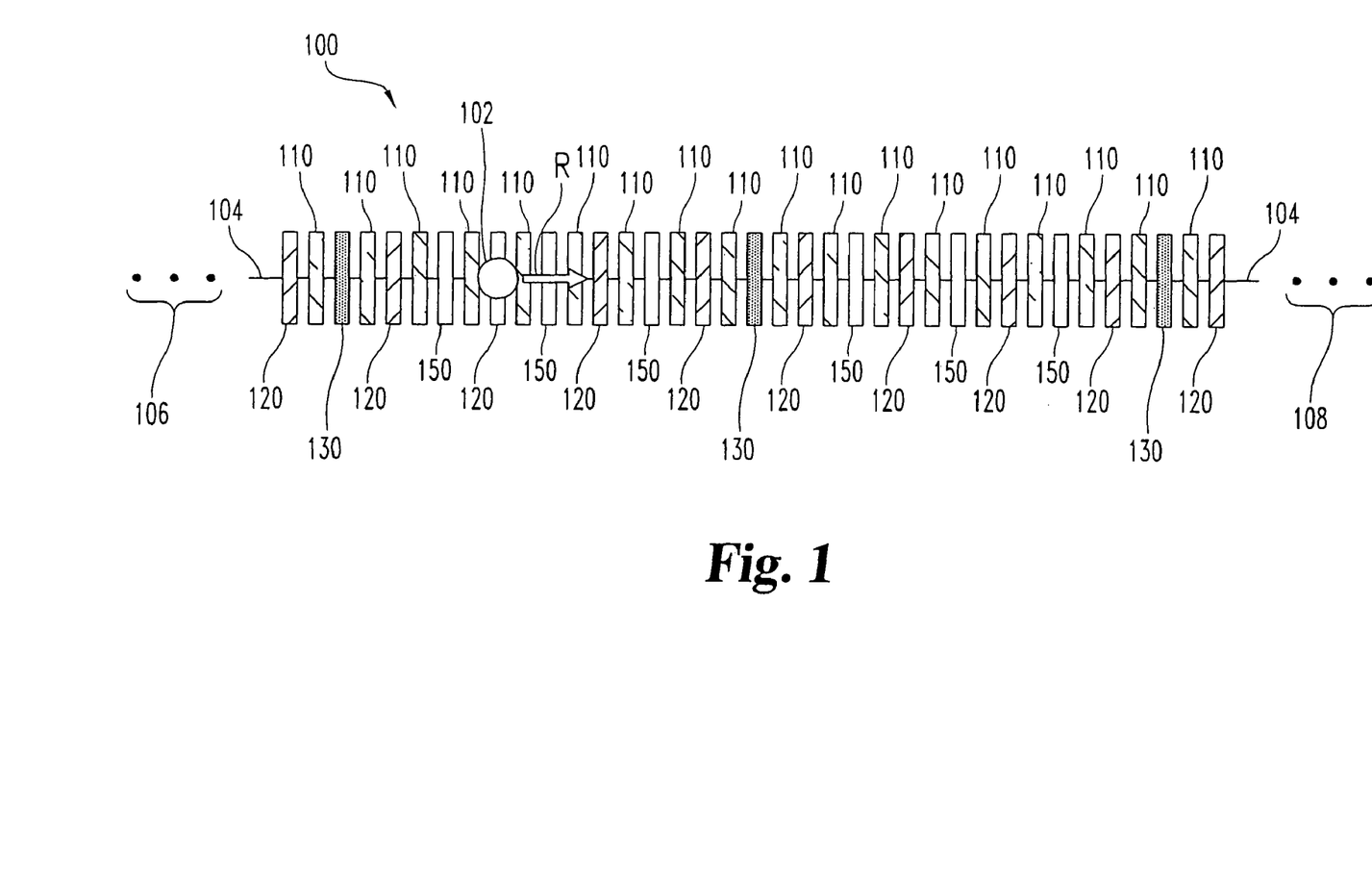
FIG. 1 is a top schematic view of a distribution of elements including multiple analyzer molecules according to one embodiment of the present invention.

With reference to FIG. 1 there is shown a distribution of elements 100 according to one embodiment of the present invention. The distribution of elements 100 includes at least three types of analyzer molecules 110, 120 and 130 distributed about scanning pathway 104 at three frequencies. Analyzer molecules 110 are distributed at a frequency of every other element of distribution 100. Analyzer molecules 120 are distributed at a frequency of every fourth element of distribution 100. Analyzer molecules 130 are distributed at a frequency of every eighth element of distribution 100. Distribution 100 also includes elements 150 which do not include analyzer molecules 110, 120, or 130. Additional types of analyzer molecules could be present at elements 150 and could, for example, be distributed at different frequencies such as every 16 elements, every 32 elements, or at other frequencies. Elements 150 could also not include analyzer molecules. As indicated by ellipses 106 and 108, elements 100 and reading pathway 104 can extend beyond the segment illustrated in FIG. 1 with the distribution of various analyzer molecules occurring at various frequencies as described above.

Scanning footprint 102 travels over the distribution of elements 100 along scanning pathway 104 in the direction indicated by arrow R. In a preferred embodiment of the present invention, the distribution of elements 100 can be about a bio-CD which is scanned with a laser beam to detect the presence or absence of analytes bound to the analyzer molecules. In one embodiment the bio-CD is preferably scanned using surface normal self referencing phase quadrature interferometry techniques. In this embodiment elements 100 might, for example, be microstructures such as radial spokes formed on the surface of the bio-CD, and analyzer molecules 110, 120, and 130 may be immobilized, for example, as monolayers, fractional monolayers, partial monolayers, or near monolayers on surfaces of the microstructures. Furthermore, scanning pathway 104 can be one of multiple substantially concentric tracks which may be scanned with a laser, for example, using interferometry techniques such as phase quadrature interferometric detection techniques. Examples of phase quadrature interferometric techniques include the micro-diffraction quadrature class ("MD-class") and adaptive optic quadrature class ("AO-class") as described in U.S. application Ser. No. 10/726,772 filed on Dec. 3, 2003 entitled "Adaptive Interferometric Multi-Analyte High-Speed Biosensor" (published on Aug. 26, 2004 as U.S. Pub. No. 2004/0166593), the contents of which are incorporated herein by reference. Other examples of phase quadrature interferometric techniques include the phase-contrast quadrature class ("PC-class") as described in U.S. Provisional Patent Application No. 60/649,070, filed Feb. 1, 2005, entitled "Phase-Contrast Quadrature For Spinning Disk Interferometry And Immunological Assay", U.S. Provisional Patent Application No. 60/755,177, filed Dec. 30, 2005, entitled "Phase-Contrast BioCD: High-Speed Immunoassays at Sub-Picogram Detection Levels", and U.S. application Ser. No. 11/345,462 being filed the same day as the present application that claims priority to these two provisional applications and entitled "Method And Apparatus For Phase Contrast Quadrature Interferometric Detection Of An Immunoassay". The disclosures of the utility application entitled "Method And Apparatus For Phase Contrast Quadrature Interferometric Detection Of An Immunoassay" is incorporated herein by reference. In these embodiments, the scanning pathway is preferably a ring shaped track of a bio-CD. During scanning the bio-CD is rotated at a scanning rate, for example, 223 revolutions per minute, to successively pass elements through the footprint of the laser beam. Under these conditions, the spatial frequency of the distribution of elements 100 corresponds to a temporal frequency.

Distribution of elements 100 is one exemplary embodiment of frequency-domain multiplexing in which different analyzer molecules are distributed at different spatial frequencies. Frequency-domain multiplexing can be used to test for many different analytes along a scanning pathway without requiring spatial separation of analyzer molecules used to detect particular analytes into sectors. In embodiments utilizing a rotating disk as a detection platform, systematics that depend on theta, the angular position about the disk, are substantially averaged out using this technique.

In addition to the embodiments described above, a variety of additional exemplary embodiments are also contemplated. For example, elements and analytes might be distributed in a variety of shapes such as substantially circular, oval, ellipsoid, square, polygonal, or other shapes. A variety of scanning pathway configurations might be utilized, including substantially linear or circular pathways, open pathways, closed pathways, curvilinear pathways, or spiral pathways, for example. A variety of frequency distributions of analyzer molecules can be used in addition to or instead of those described above. A variety of spacing of elements or analyzer molecules may also be used, for example, successive elements or analyzer molecules may be adjacent or adjoining, or may be spaced at intervals differing from those shown in connection with FIG. 1, or may overlap or occupy the same position. A variety of substrates and platforms may also be used including disks or chips supporting planar arrays including, for example, those described herein. Additionally, the variations and additional embodiments described elsewhere herein may apply to the present embodiment.

Figure 2:
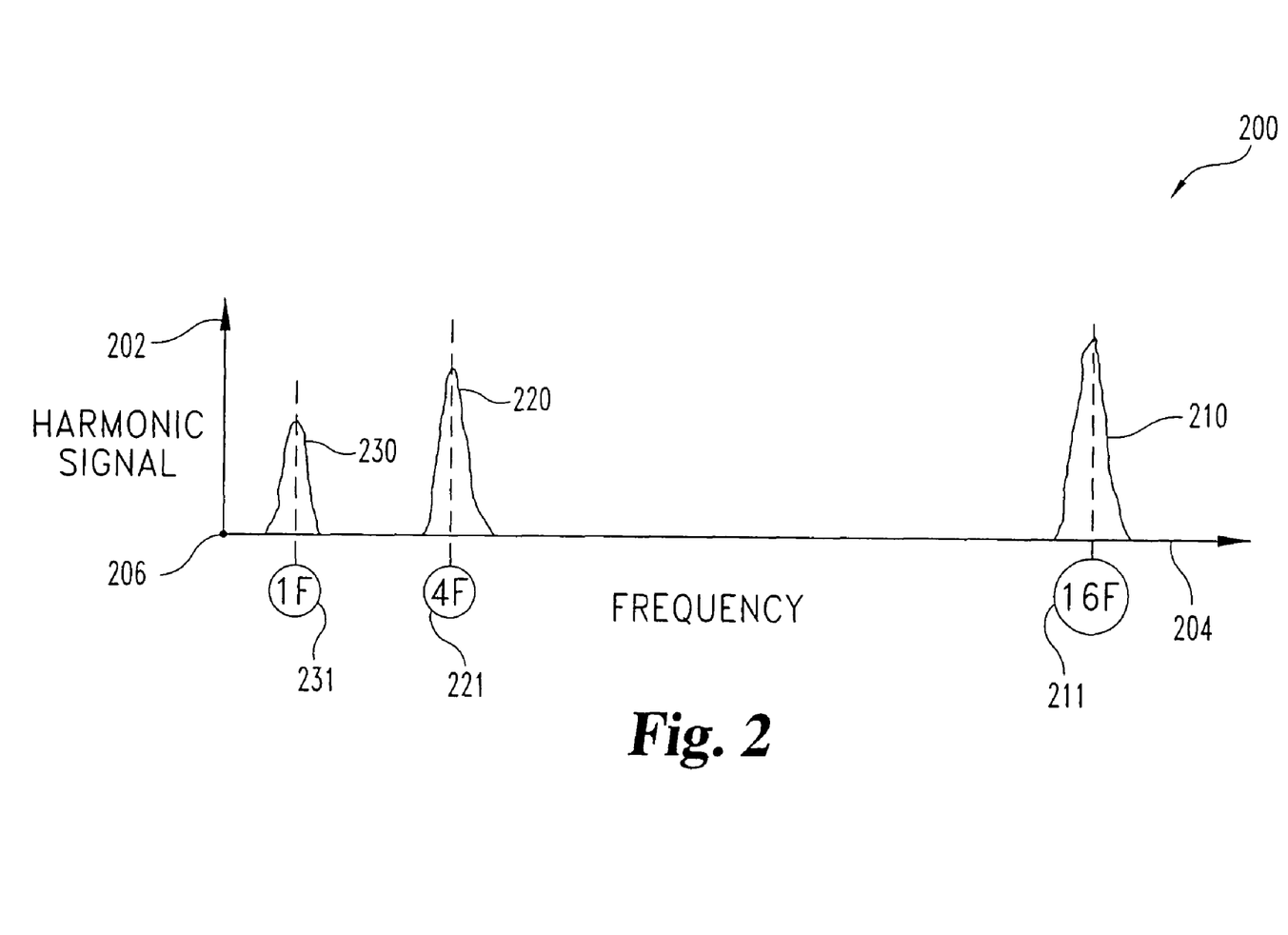
FIG. 2 is a graph illustrating harmonic signals indicating the detection of analytes by the analyzer molecules of FIG. 1.

With reference to FIG. 2 there is shown graph 200 illustrating an example of detection of target analytes using the distribution of elements 100 illustrated and described in connection with FIG. 1. The x axis of graph 200 is frequency which increases from origin 206 in the direction indicated by x axis arrow 204. The y axis of graph 200 is harmonic signal intensity which increases from origin 206 in the direction indicated by y axis arrow 202.

As shown in FIG. 2, the results of a scanning of the distribution of elements 100 can be represented in the frequency domain. Harmonic signals 210, 220 and 230 indicate detection of binding of target analytes to analyzer molecules 110, 120, and 130, respectively. Signal 230 has center frequency 231, signal 220 has center frequency 221, and signal 210 has center frequency 211. Center frequencies 231, 221, and 211 correspond to the spatial frequencies of analyzer molecules 130, 120, and 110, respectively, and the rate of scanning. Since the spatial frequency of analyzer molecules 110 is 16 times that of analyzer molecules 130 and 4 times that of analyzer molecules 120, the harmonic signal 210 has a center frequency 211 sixteen times that of the center frequency 231 of harmonic signal 231 and four times that of center frequency 221 of harmonic signal 220. Detection of signals at a variety of different frequencies corresponding to spatial frequencies of analyzer molecules is possible. Furthermore, time domain detection techniques can be utilized.

Figure 3:
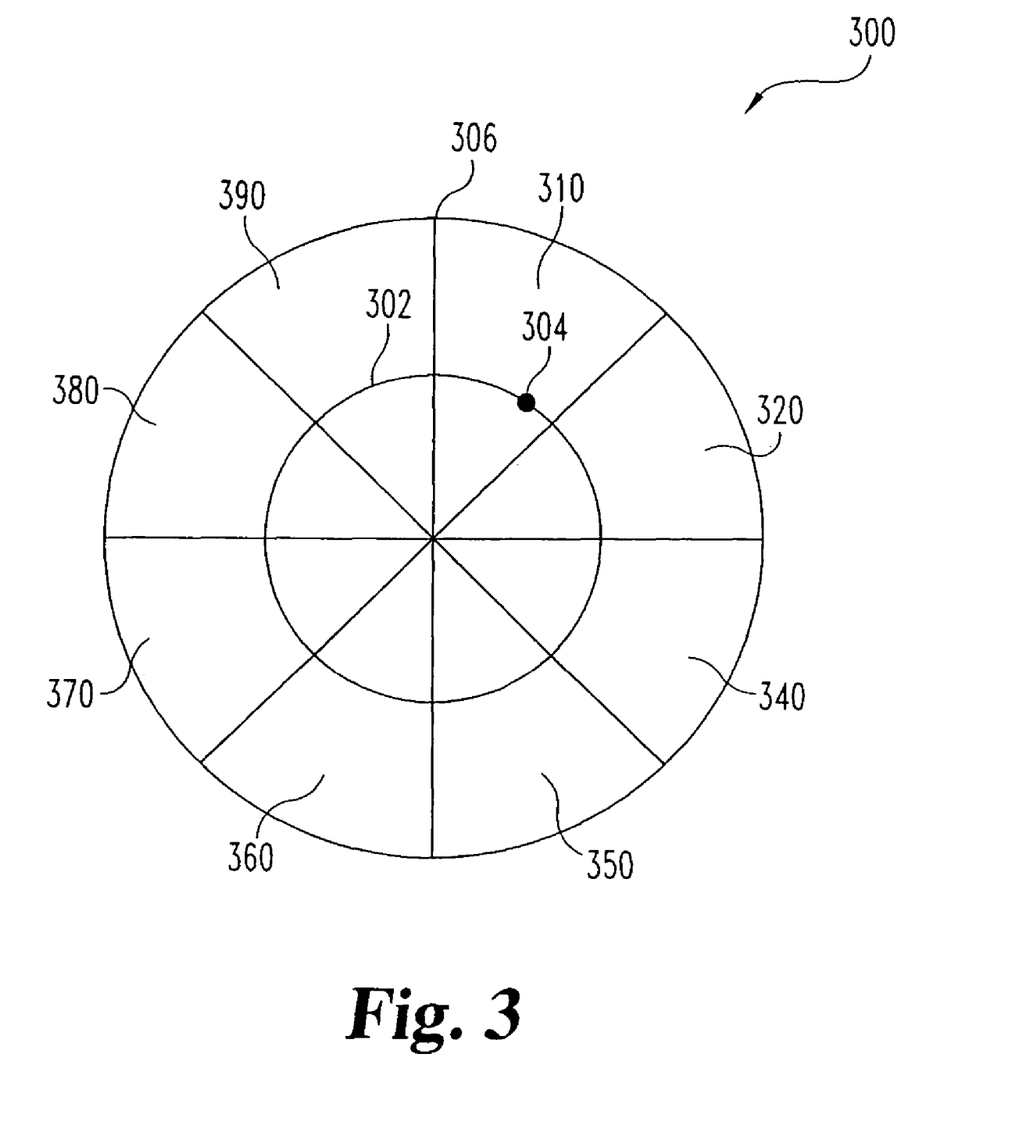
FIG. 3 is a top schematic view of a bio-CD according to one embodiment of the present invention.

With reference to FIG. 3 there is shown a bio-CD 300 according to another embodiment of the present invention. Bio-CD 300 includes sectors 310, 320, 330, 340, 350, 360, 370, 380 and 390. A substantially circular scanning pathway 302 is defined about the read surface of Bio-CD 300 and scanning footprint 304 follows pathway 302 when bio-CD 300 is rotated. Bio-CD 300 may also include multiple other scanning pathways substantially concentric with pathway 302 located inside the outer perimeter 306 of bio-CD 300. Additionally, bio-CD 300 may include an aperture located at its center for receiving a device used to rotate bio-CD 300.

Each of sectors 310, 320, 330, 340, 350, 360, 370, 380 and 390 could include a different type of analyzer molecule to test for a different analyte in a single sample, or could include the same type of analyzer molecule and test different samples for the same analyte. Combinations of these two examples are also possible, for example, the eight sectors shown in FIG. 3 could be used to test two samples for four different analytes, four samples for two different analytes, two samples for one analyte and two samples for three analytes, one sample for one analyte another sample for two analytes and another sample for five analytes, or various other combinations using all or some of the sectors for various other combinations of analyzer molecule(s) and test sample(s).

In a preferred embodiment according to the present invention, a bio-CD including a plurality of tracks as reading pathways provides a platform that can be divided into sectors as described above and used in a surface normal self referencing phase quadrature interferometric detection system. One such embodiment preferably includes 1024 interferometric elements per track and is divided into sixteen sectors for receiving sixteen samples. The total number of assays in this case is sixteen times the number of tracks. At 1000 tracks this allows 16,000 assays. Another such preferred embodiment includes 8192 interferometric elements per track and is divided into 128 sectors for receiving 128 samples. The total number of assays in this case is 128 times the number of tracks. For 1000 tracks, this is 128,000 assays. Thus, very high numbers of assays may be conducted in the time required to scan a bio-CD, which can be as little as about twenty minutes or less.

Figure 4:
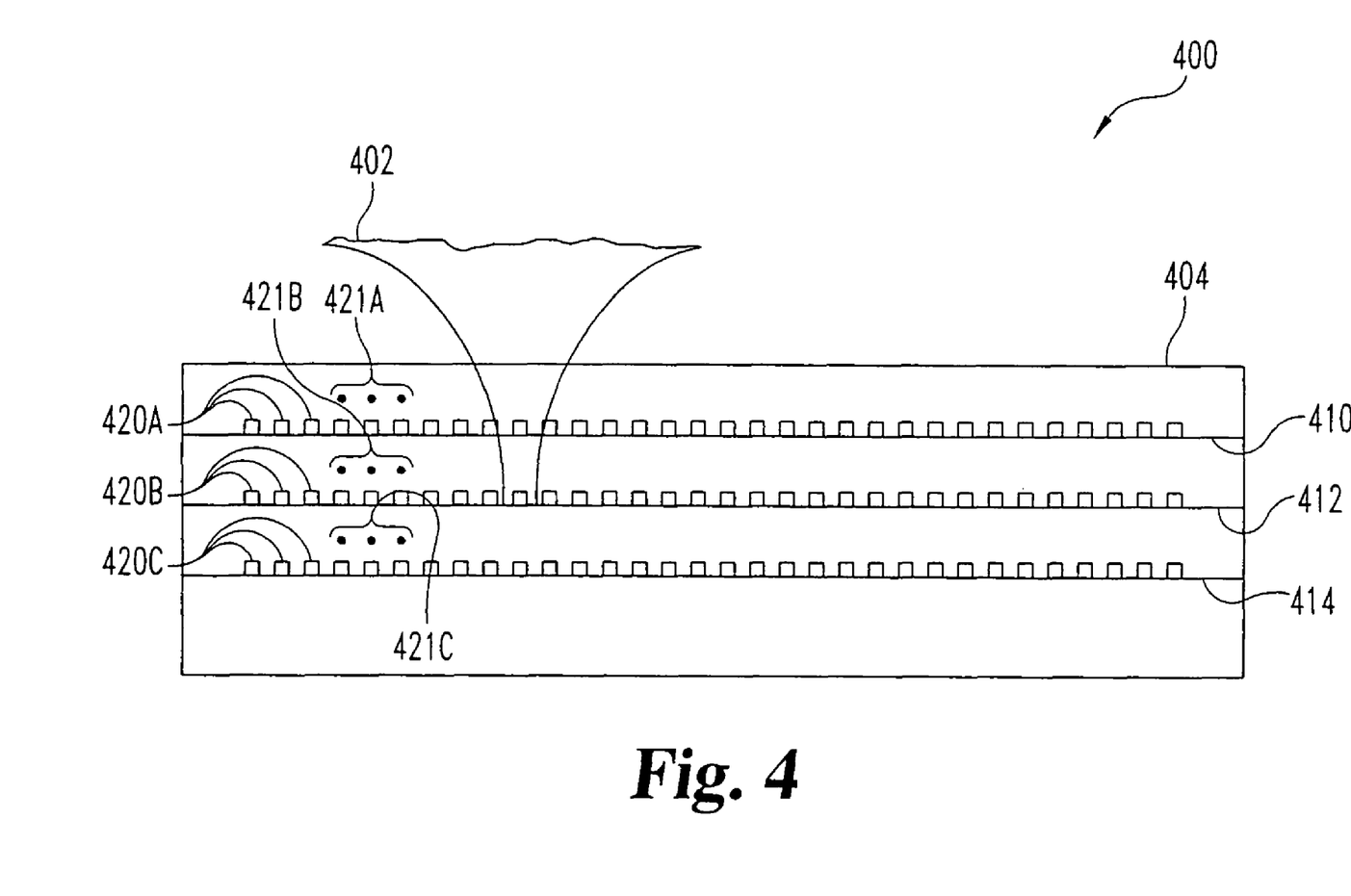
FIG. 4 is a side sectional schematic view of a biosensor platform according to one embodiment of the present invention.

With reference to FIG. 4 there is shown a multi-layer biosensor platform 400 according to one embodiment of the present invention. Platform may be a disk or chip including, for example, those described herein. Platform 400 includes an upper surface 404 and scanning levels 410, 412, and 414 which are positioned at different distances from surface 404. Scanning levels 410, 412, and 414 include interferometric elements 420A, 420B, and 420C, respectively. For simplicity, only a few interferometric elements are labeled, but additional interferometric elements are present as indicated by ellipses 421A, 421B, and 421C. Analyzer molecules may be provided on scanning surfaces of interferometric elements 420A, 420B, and 420C, and may be exposed to test samples via microfluidic channels internal to platform 400. Confocal microscope optics can be used to direct a laser beam 402 to scan interferometric elements 420A, 420B, and 420C. As shown in FIG. 4 laser beam 402 is scanning elements 420B of level 412. Thus, it is possible to isolate a signal from a specific scanning level of platform 400.

In a preferred embodiment of the present invention platform 400 is a multi-level bio-CD. In this embodiment, the interferometric elements can be transparent or partially transparent elements, placed in a stack at different levels in a fashion similar to that of a high-density DVD. To focus at a different level, the disk is moved to or away from the objective, or else the optical train is moved toward or away from the disk or chip.

The embodiments described above in connection with FIGS. 3 and 4 are examples of space domain multiplexing in which spatially separate segments of a biosensor platform carry different analytes. Additionally, the variations and additional embodiments described elsewhere herein may apply to the present embodiment.

Figure 5:
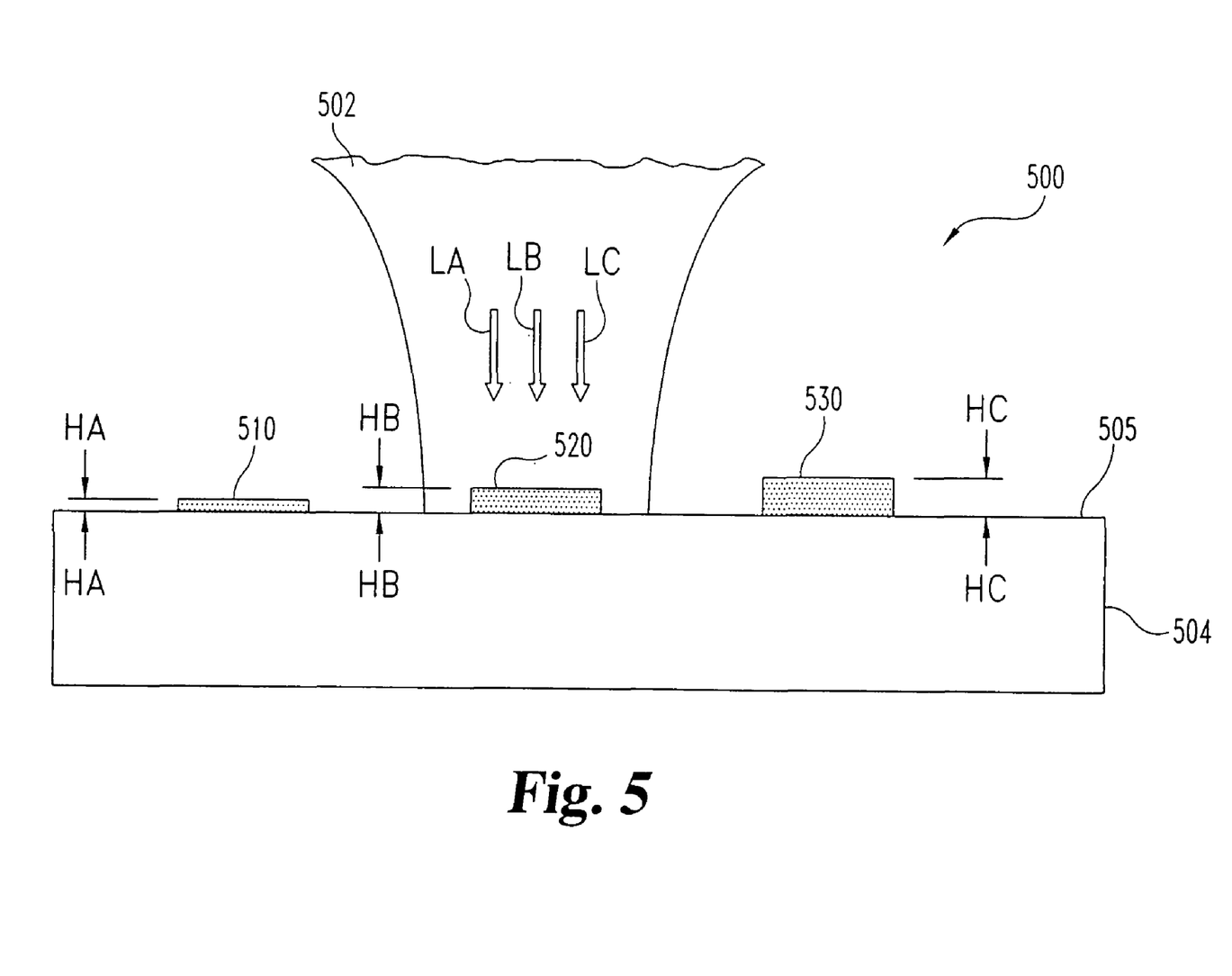
FIG. 5 is a side sectional schematic view of a biosensor platform according to one embodiment of the present invention.

With reference to FIG. 5 there is shown a biosensor platform 500 according to one embodiment of the present invention. Platform 500 includes substrate 504 having upper surface 505. Microstructures 510, 520 and 530 are disposed on surface 505 and have a variety of heights. Microstructures 510, 520 and 530 and are scanned by laser beam 502. Laser beam 502 preferably includes a plurality of wavelengths of laser light represented by arrows LA, LB, and LC. The height of microstructure 510 shown by arrows HA is ⅛ wavelength LA, the height of microstructure 520 shown by arrows HB is ⅛ wavelength LB, and the height of microstructure 530 shown by arrows HC is ⅛ wavelength LC. Thus, microstructures 510, 520, and 530 are individually tuned to produce a phase quadrature condition for the different wavelengths LA, LB, and LC, respectively. As described above, each of microstructures 510, 520, and 530 could include a different analyzer molecule immobilized to its surface for detecting a different analyte. It is also contemplated that additional or fewer microstructure heights and/or light wavelengths could be used.

The embodiments shown and described above in connection with FIG. 5 is one example of wavelength-domain multiplexing which includes having multiple types of microstructures on a single track that are individually tuned to different wavelengths. A variety of additional embodiments and variations are also contemplated. In a preferred embodiment according to the present invention biosensor platform 500 is a bio-CD and the scanning of elements is accomplished by rotating the bio-CD to pass the interferometric microstructures through the footprint of the laser beam. In this embodiment microstructures can be radial spokes formed at different heights. The heights can be selected so that a microstructure is in quadrature for one wavelength, but null for a different wavelength. Furthermore, the distribution of analyzer molecules about the microstructures can be according to frequency-domain multiplexing, space-domain multiplexing or code-domain multiplexing schemes including those described above and below.

In other embodiments according to the present invention different height microstructures are not required, rather a laser probe contains a continuum of wavelengths, and readout in the far field can use an imaging spectrometer to separate theta and wavelength, for example, or readout can use interferometry techniques. In one preferred embodiment according to the present invention a phase contrast bio-CD provides an interferometry platform including a multiplexed distribution of analyzer molecules without different height microstructures. This phase contrast platform can be scanned with a plurality of wavelengths to define quadrature conditions and quadrature angles. Different wavelengths interact differently with this phase contrast platform and can be separated during detection to extract independent information from the wavelengths, for example, using interferometry. Multiple discrete wavelengths can be utilized or one or more wavelength continuums can be utilized. Other exemplary platforms not including different height microstructures include surface plasmon resonance platforms including a multiplexed distribution of analyzer molecules. Scanning of such platforms with multiple wavelengths can be read out as angular shifts or as frequency shifts.

Wavelength-domain multiplexing techniques allow probing at many different wavelengths, bringing spectroscopic molecular specificity to bear on the laser-scanning interferometry. There can be significant information contained in the spectral absorption of biomolecules. This information can be used in detecting target analytes in a sample. Additionally, the variations and additional embodiments described elsewhere herein may apply to the present embodiment.

Figure 6:
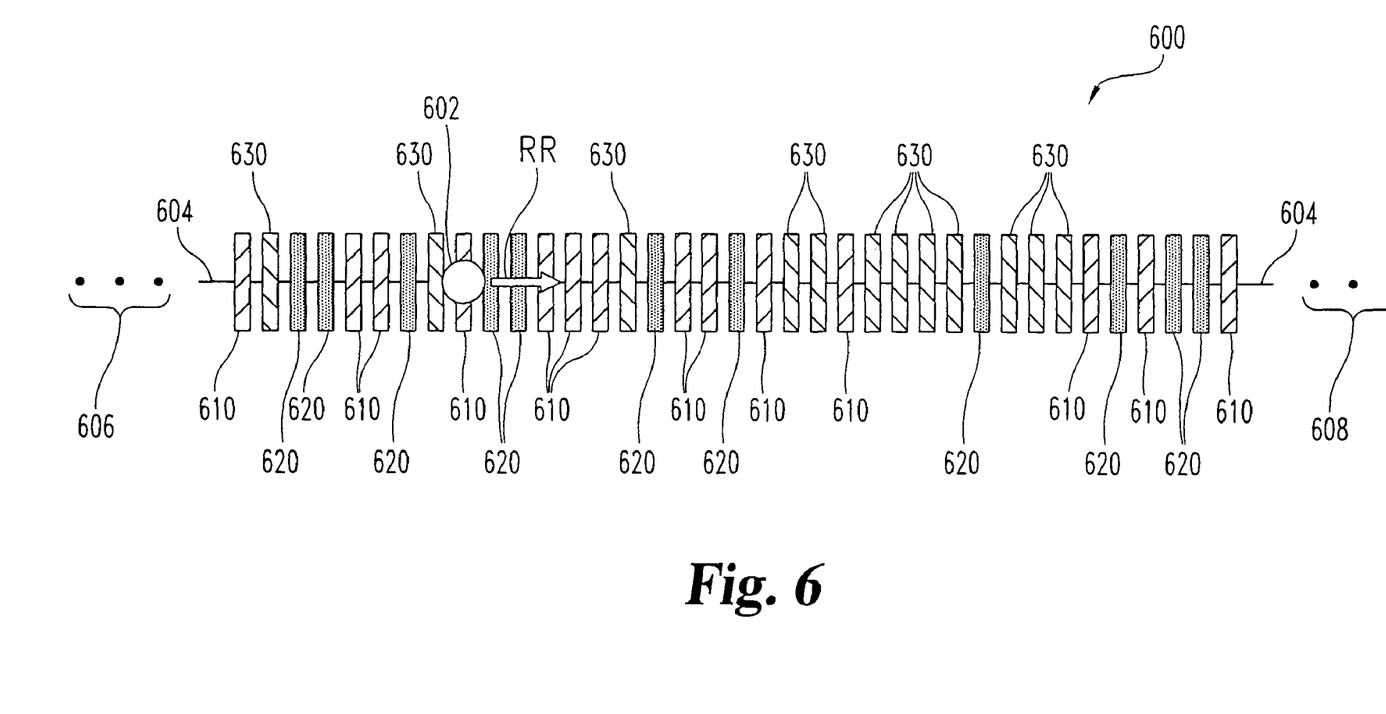
FIG. 6 is a top schematic view of a distribution of elements including multiple analyzer molecules according to one embodiment of the present invention.

With reference to FIG. 6 there is shown a distribution of elements 600 according to another embodiment of the present invention. The distribution of elements 600 includes three types of analyzer molecules 610, 620 and 630 distributed about scanning pathway 604 according to a pseudorandom sequence or a random sequence. As indicated by ellipses 606 and 608, elements 600 and reading pathway 604 can extend beyond the segment illustrated in FIG. 6 with the distribution of various analyzer molecules occurring pseudorandomly or randomly as described above.

Scanning footprint 602 travels over the distribution of elements 600 along scanning pathway 604 in the direction indicated by arrow RR. In a preferred embodiment of the present invention, the distribution of elements 600 can be on a bio-CD which is scanned with a laser beam to detect the presence or absence of analytes bound to the analyzer molecules preferably using surface normal self referencing phase quadrature interferometry techniques. In this embodiment elements 600 may be microstructures such as radial spokes formed on the surface of the bio-CD and analyzer molecules 610, 620, and 630 may be immobilized as monolayers, fractional monolayers, partial monolayers, or near monolayers on surfaces of the microstructures. Alternatively, in this and other embodiments, the elements may be defined regions on a substrate without microstructures. Furthermore, scanning pathway 604 can be one of multiple substantially concentric tracks which may be scanned with a laser, for example, as described above. In this embodiment, the scanning pathway is preferably a substantially ring shaped track of a bio-CD.

Figure 7:
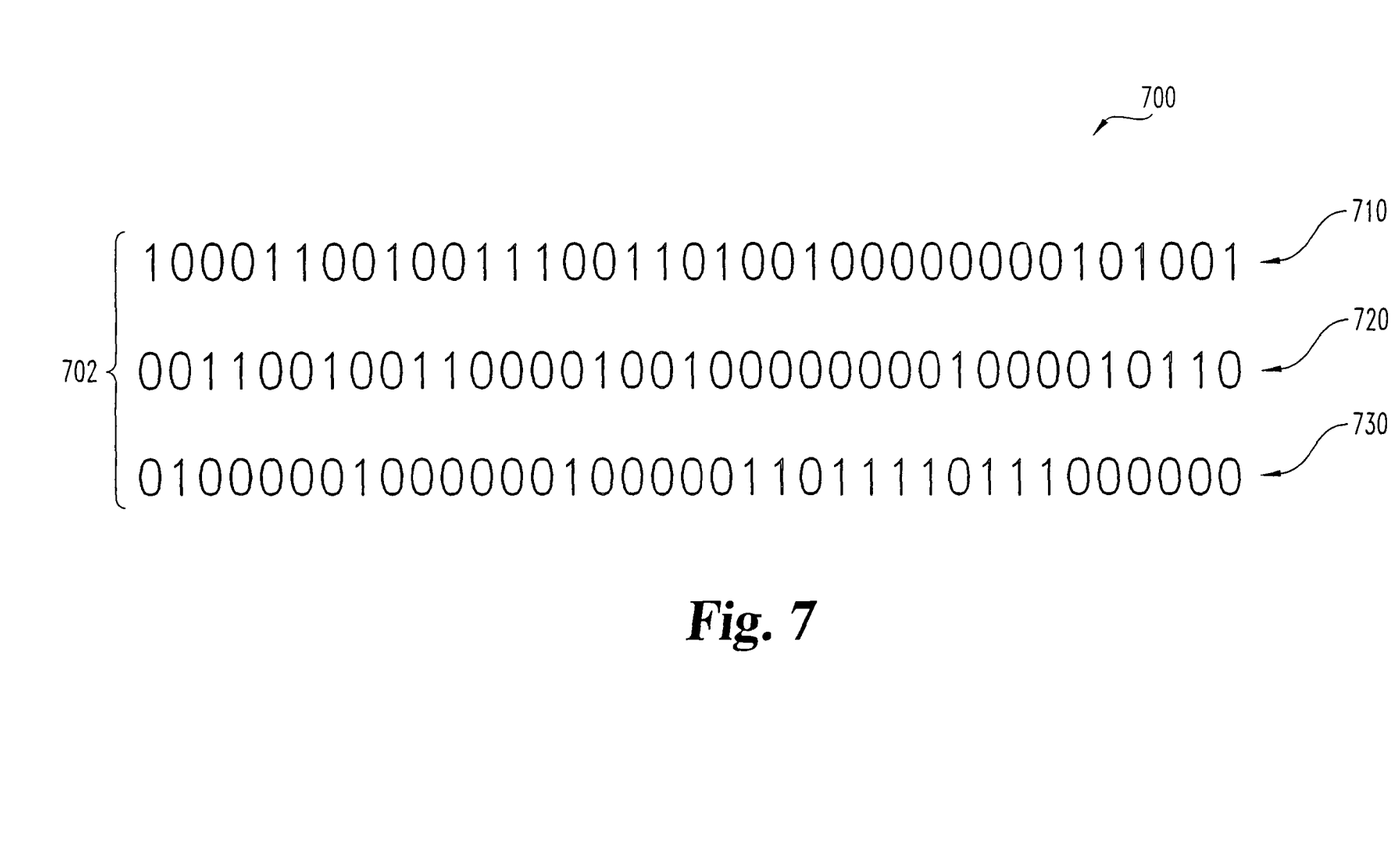
FIG. 7 is a view of orthogonal bit sequences relating to the distribution of elements of FIG. 6.

Scanning of distribution of elements 600 can yield a multiplexed bit sequence which can be processed using known orthogonal bit sequence, for example with matched gating techniques, to produce bit sequences corresponding to each analyzer molecule. FIG. 7 shows a group of mutually orthogonal bit sequences 702 corresponding to the occurrences of analyzer molecules 610, 620, and 630 shown and described above in connection with FIG. 6. Orthogonal bit sequence 710 corresponds to the occurrences of molecules 610, orthogonal bit sequence 720 corresponds to the occurrences of molecules 620, and orthogonal bit sequence 730 corresponds to the occurrences of molecules 630.

Distribution of elements 600 is one exemplary embodiment of code-division multiplexing in which different analyzer molecules are distributed according to a known pseudorandom or random sequence. A variety of additional exemplary embodiments are also contemplated. For example, greater numbers of analyzer molecules could be used. Additionally, the variations and additional embodiments described above and below may also apply to the present embodiment.

Various embodiments according to the present invention can include a variety of biosensor platforms including those described above. For example, these platforms include bio-CDs such as micro-diffraction bio-CDs, adaptive-optical bio-CDs, phase-contrast bio-CDs, and others. Details relating to these various classes of bio-CDs can be found, for example, in the aforementioned patent applications incorporated herein by reference. These platforms further include bio-chips, immunological chips, gene chips, DNA arrays, platforms used in connection with fluorescence assays and other platforms and substrates supporting planar arrays including analyzer molecules.

Various embodiments according to the present invention can include a variety of analyzer molecules useful in detecting the presence or absence of a variety of target analytes in a solution to be tested. For example, these analyzer molecules can include antibodies or immunoglobulins, antigens, DNA fragments, cDNA fragments, aptameres, peptides, proteins, and other molecules. Various embodiments according to the present invention can include combinations of one or more the foregoing and other types of analyzer molecules known to those of ordinary skill in the art arranged, for example, in a planar array.

Various embodiments according to the present invention can be used in connection with a variety of scanning and detection techniques. For example, such techniques include interferometry, including surface normal interferometry techniques, and preferably phase quadrature interferometry techniques where one detected optical mode differs in phase from another by about $\pi/2$ or an odd integer multiple thereof, and/or self referencing interferometry techniques where a reference wave is generated locally with respect to a signal wave so that the reference and signal waves experience common aberrations and path length changes and thus maintain a constant relative phase without the need for active stabilization of different light paths, florescence techniques and platforms, resonance techniques and platforms, and other techniques and platforms.

As used herein terms relating to properties such as geometries, shapes, sizes, physical configurations, speeds, rates, frequencies, periods, amplitudes, include properties that are substantially similar or about the same or equal to the properties described unless explicitly indicated to the contrary.

While the invention has been illustrated and described in detail in the drawings and foregoing description, the same is to be considered as illustrative and not restrictive in character, it being understood that only preferred embodiments have been shown and described and that all changes and modifications that come within the spirit of the invention are desired to be protected.

What is claimed is:

1. A method for determining the presence or absence of biological material in a sample comprising:
multiplexing a plurality of kinds of capture molecules about a detection pathway on a planar array, comprising the steps of:
distributing a first kind of capture molecule along the detection pathway at a first spatial frequency,
interspersing a second kind of capture molecule among the first kind of capture molecule along the detection pathway at a second spatial frequency, and
interspersing a third kind of capture molecule among the first and second kinds of capture molecules along the detection pathway at a third spatial frequency, each of the first, second and third spatial frequency being different from the other of the first, second and third spatial frequencies;

contacting a biological sample to the planar array;

scanning the planar array along the detection pathway with a scanning beam traveling over the plurality of kinds of capture molecules to produce a reflected beam containing information from the plurality of kinds of capture molecules; and detecting the presence or absence of binding of the plurality of kinds of capture molecules and a plurality of target analytes using interferometry and by demultiplexing the reflected beam containing information from the plurality of kinds of capture molecules to determine information of a particular capture molecule.

2. The method of claim 1 wherein the detecting further comprises detecting a first binding using a first wavelength of laser light and a second binding using a second wavelength of laser light.

3. The method of claim 1 wherein the detection pathway is defined along a surface of a bio-optical disk.

4. The method of claim 1 further comprising rotating the pathway in connection with the detecting.

5. The method of claim 1 wherein the detecting uses self-referencing phase quadrature interferometry.

6. The method of claim 1 further comprising demultiplexing information of a particular capture molecule and a particular target analyte in connection with the detecting.

7. The method of claim 1 wherein the first kind of capture molecule is adapted to selectively bind a first type of target analyte.

8. The method of claim 1 wherein the plurality of kinds of capture molecules are selected from at least one of binding cells, viruses, bacteria, toxins, peptides, DNA fragments and antibodies.

9. A method for determining the presence or absence of a plurality of target analytes in a biological sample comprising:

obtaining a substrate having a surface with a detection pathway with a first type of biological recognition molecule and a second type of biological recognition molecule frequency-domain multiplexed, wavelength domain multiplexed or code-division multiplexed thereabout, the first type of biological recognition molecule being distributed at a first spatial frequency and the second type of biological recognition molecule being interspersed with the first type of biological recognition molecule along the detection pathway and being distributed at a second spatial frequency, the second spatial frequency being different from the first spatial frequency;

exposing the surface of the substrate to the biological sample;

directing a probe laser beam at the surface of the substrate;

scanning the probe laser beam across at least the detection pathway; and detecting binding of the first type of biological recognition molecule to at least one of the target analytes using a first wavelength of laser light and binding of the second type of biological recognition molecule to at least another one of the target analytes using a second wavelength of laser light.

10. The method of claim 9 wherein the detection pathway is defined along a surface of a bio-optical disk.

11. The method of claim 9 further comprising rotating the detection pathway to detect the binding of the first and second types of biological recognition molecules.

12. The method of claim 9 wherein the detection step includes an interferometric detection process.

13. The method of claim 12 wherein the interferometric detection process includes a self-referencing phase quadrature interferometric process.

14. The method of claim 9 further comprising demultiplexing information of a particular biological recognition molecule and a particular target analyte in connection with the detection step.

15. The method of claim 9 wherein the biological recognition molecules are selected from at least one of binding cells, viruses, bacteria, toxins, peptides, DNA fragments and antibodies.

16. The method of claim 1, wherein the first kind of capture molecules are disposed at a first height relative to the planar array and the second kind of capture molecules are disposed at a second height relative to the planar array, the first height being different from the second height; and wherein the detecting step further comprises:

detecting a first binding using a first wavelength of light, the first height being tuned to produce a phase quadrature condition for the first wavelength of light; and detecting a second binding using a second wavelength of light, the second height being tuned to produce a phase quadrature condition for the second wavelength of light.

17. The method of claim 1, wherein the multiplexing is frequency-domain multiplexing, wavelength domain multiplexing or code-division multiplexing.

18. The method of claim 9, wherein the first type of biological recognition molecule is positioned at a first height relative to the surface of the substrate, and the second type of biological recognition molecule is positioned at a second height relative to the surface of the substrate, the first height being different from the second height.

19. A method for determining the presence or absence of biological material in a sample comprising:

multiplexing a plurality of kinds of capture molecules about a detection pathway on a planar array comprising the steps of:

distributing a first kind of capture molecule along the detection pathway at a first spatial frequency, interspersing a second kind of capture molecule among the first kind of capture molecule along the detection pathway at a second spatial frequency, and interspersing a third kind of capture molecule among the first and second kinds of capture molecules along the detection pathway at a third spatial frequency, each of the first, second and third spatial frequency being different from the other of the first, second and third spatial frequencies;

contacting a biological sample to the planar array;

scanning the planar array along the detection pathway with a scanning beam traveling over the plurality of kinds of capture molecules to produce a reflected beam containing information from the plurality of kinds of capture molecules; and detecting the presence or absence of binding of the plurality of kinds of capture molecules and a plurality of target analytes using interferometry and by demultiplexing the reflected beam containing information from the plurality of kinds of capture molecules to determine information of a particular capture molecule, wherein the demultiplexing the reflected beam comprises using the first, second and third spatial frequencies to detect the presence or absence of binding of the first, second and third kinds of capture molecules, respectively, with the plurality of target analytes.

* * * * *